US006346625B1

(12) United States Patent
Karabelas et al.

(10) Patent No.: US 6,346,625 B1
(45) Date of Patent: Feb. 12, 2002

(54) PROTEIN KINASE INHIBITORS

(75) Inventors: Kostas Karabelas; Matti Lepistö; Peter Sjö, all of Lund (SE)

(73) Assignee: AstraZeneca AB (SE)

( * ) Notice: Subject to any disclaimer, the term of this patent is extended or adjusted under 35 U.S.C. 154(b) by 0 days.

(21) Appl. No.: 09/403,720

(22) PCT Filed: Jun. 23, 1999

(86) PCT No.: PCT/SE99/01145

§ 371 Date: Oct. 25, 1999

§ 102(e) Date: Oct. 25, 1999

(87) PCT Pub. No.: WO00/02877

PCT Pub. Date: Jan. 20, 2000

(51) Int. Cl.[7] .................... C07D 403/04; C07D 403/14; C07D 409/14; A61K 31/4178
(52) U.S. Cl. ..................................... 548/312.1; 514/397
(58) Field of Search ........................ 548/312.1; 514/397

(56) References Cited

U.S. PATENT DOCUMENTS

| | | | |
|---|---|---|---|
| 3,642,803 A | 2/1972 | Welstead, Jr. | 260/293.61 |
| 3,821,389 A | 6/1974 | Grivas | 424/270 |
| RE28,973 E | 9/1976 | Welstead, Jr. | 260/293.61 |
| 4,031,221 A | 6/1977 | Helsley et al. | 424/267 |
| 4,062,869 A | 12/1977 | Weston | 260/326.16 |
| 4,466,976 A | 8/1984 | Klose et al. | 424/273 |
| 4,532,250 A | 7/1985 | Stout et al. | 514/341 |
| 4,585,771 A | 4/1986 | Klose et al. | 514/220 |
| 4,598,079 A | 7/1986 | Beyerle et al. | 514/252 |
| 4,912,125 A * | 3/1990 | Huebner et al. | 514/402 |
| 5,057,614 A | 10/1991 | Davis et al. | 548/466 |
| 5,077,293 A | 12/1991 | Smith et al. | 514/253 |
| 5,192,770 A | 3/1993 | Clark et al. | 514/305 |
| 5,380,746 A | 1/1995 | Barth et al. | 514/414 |
| 5,399,712 A | 3/1995 | Hill | 578/455 |
| 5,466,699 A * | 11/1995 | Robertson et al. | 514/323 |
| 5,516,915 A | 5/1996 | Barth et al. | 548/455 |
| 5,545,636 A | 8/1996 | Heath et al. | 514/214 |
| 5,612,362 A * | 3/1997 | MacLeod | 514/392 |
| 6,054,590 A * | 4/2000 | Poindexter et al. | 548/311.1 |
| 6,153,641 A | 11/2000 | Bergstrand et al. | 514/414 |

FOREIGN PATENT DOCUMENTS

| | | |
|---|---|---|
| DE | 3141063 A1 | 4/1983 |
| EP | 0328026 A1 | 2/1989 |
| EP | 0464604 A2 | 1/1992 |
| EP | 0490263 A1 | 6/1992 |
| EP | 0540956 A1 | 11/1993 |
| EP | 0675125 A1 | 10/1995 |
| FR | 7311450 | 3/1973 |
| GB | 1500176 | 2/1978 |
| SU | 389096 | 9/1973 |
| WO | WO93/18765 | 9/1993 |
| WO | WO95/17182 | 6/1995 |
| WO | WO 96/01825 | 1/1996 |
| WO | WO 98/13368 | 4/1998 |
| WO | WO 98/43632 | 10/1998 |
| WO | WO99/32483 | 7/1999 |

OTHER PUBLICATIONS

Bergstrand et al., "Modulation of Neutrophil Superoxide Generation by Inhibitors of Protein Kinase C, . . . " The Journal of Pharmacology and Experimental Therapeutics, vol. 263, No. 3, pp. 1334–1346.

Chakravarthy et al., "The Direct Measurement of Protein Kinase C (PKC) Activity in Isolated Membranes Using a Selective Peptide Substrate", Analytical Biochemistry, 1991, vol. 196, pp. 144–150.

Gazit et al., "Tyrphostins. 5. Potent Inhibitors of Platelet–Derived Growth Factor Receptor Tyrosine Kinase: Structure–Activity Relationships . . . ", J. Med. Chem., 1996, vol. 39, pp. 2170–2177.

Granet et al., "A Microtiter Plate Assay for Protein Kinase C[1]", Analytical Biochemistry, 1987, 163:458–463.

Olsson et al., Activation of Human Neutrophil Protein Kinase C in vitro by 1, 2–isopropylidene–3–decanoyl–sn–glcerol (Ip (COC$_9$), Cellular Signaling, 1989, 1(4) :405–410.

Galzunov et al., "Investigation of the Riboflavine Operon of Bacillus Subtilis V11. Biochemical Study of Mutants Relating to Early Stages of Biosynthesis" Translated from Genetika 10(11):83–92, 1974, see Chemical Abstracts vol. 82 No. 13 (1975) abstract 82817b.

Elisabete R. Pereira et al., "Synthesis and Biological Evaluation of Monoindolyl and Indolocarbazolyl Oxazolones and Imidazolones", Chem. Pharm. Bull. 45(4) 733–736, Pharmaceutical Study Of Japan: 1997.

(List continued on next page.)

*Primary Examiner*—Floyd D. Higel
(74) *Attorney, Agent, or Firm*—Fish & Richardson PC

(57) ABSTRACT

The present invention relates to compounds of formula (I)

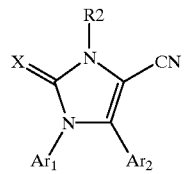

(I)

wherein:

Ar$_1$ or Ar$_2$ is an optionally substituted indole, and the other group is an optionally substituted aromatic or heteroaromatic group, preferably an optionally substituted indole, X is O or S, and R2 is H, hydroxy, amino, C$_{1-6}$alkyl, hydroxyC$_{1-6}$alkyl or aminoC$_{1-6}$alkyl, and salts and solvates thereof and solvates of such salts, and the use of such compounds in medical therapies.

45 Claims, No Drawings

OTHER PUBLICATIONS

Patent Abstracts of Japan: vol. 14 No. 459 (C–767) (4402); Oct. 4, 1990.

Yuji Oikawa et al., "Synthesis of Pimprinine And Related Oxazolylindole Alakaloids From N–ACYL Derivatives Of Tryptamine And Methyl Ester By DDQ Oxidation", Heterocycles. vol. 12. No. 11, 1979.

Carmen Galvez et al., "A Conveinent Preparation of Haloaminobenzo[b]thiophene Derivatives", Communications (932–933); Nov. 1983.

Thomas W. von Geldern et al., "Azole Endothelin Antagonists. 1. A Receptor Model Explains an Unusual Structure–Activity Profile", J. Med. Chem. 1996, 39, 957–967.

J. Bergman et al., "Synthesis And Reactions Of Some 3–(2–Haloacyl) indoles", Tetrahedron. vol. 29, pp. 971–976; Pergamon Press 1973.

* cited by examiner

PROTEIN KINASE INHIBITORS

FIELD OF THE INVENTION

The present invention relates to novel compounds which are protein kinase C inhibitors, methods for their preparation, intermediates therefor and pharmaceutical compositions comprising them.

BACKGROUND OF THE INVENTION

Protein kinase C (PKC) is a family of phospholipid-dependent serine/threonine-specific protein kinases which play an important role in cellular growth control, regulation and differentiation.

Since the activation of PKC has been implicated in several human disease processes, including various forms of cancer, different forms of inflammatory and/or immunological disorders as well as some neurological disorders, inhibition of PKC could be of therapeutic value in treating these conditions.

Several classes of compounds have been identified as PKC inhibitors, e.g. isoquinoline sulfonamides, sphingosine and related sphingolipids, indolocarbazoles and bisindolylmaleimides.

EP 0 328 026 describes the use of certain bisindolylmaleimides, a class of compounds related to the indolocarbazoles, in medicaments for the treatment of various conditions.

SU 389096 to Baskakov et al describes 1.5 substituted diphenyl imidazolones although these are not suggested to be of any therapeutic potential.

Although PKC inhibitors are described in the prior art, there is a need for specific anti-inflammatory and immunosuppressive compounds which are suitable for oral administration, and for inhalation. Furthermore, there is a need for such compounds which are more soluble and less colored than the presently known PKC inhibitors.

SUMMARY OF THE INVENTION

The present invention provides kinase inhibitors which are particularly PKC inhibitors, methods for their preparation and intermediates used for their preparation.

The kinase inhibitors of the present invention are surprisingly more soluble and less colored than the kinase inhibitors, especially the PKC inhibitors, known in the prior art.

The present invention also provides the use of the compounds of the present invention for the treatment of inflammatory, immunological, bronchopulmonary, cardiovascular, oncological or CNSdegenerative disorders.

Also provided by the present invention are pharmaceutical compositions comprising a compound according to the present invention, as active ingredient, together with a pharmaceutically acceptable adjuvant, diluent or carrier.

DETAILED DESCRIPTION OF THE INVENTION

The present invention provides compounds of formula (I)

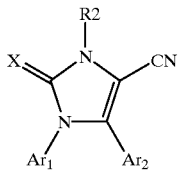

(I)

wherein:
$Ar_1$ or $Ar_2$ is an optionally substituted indole, and the other group is an optionally substituted aromatic or heteroaromatic group, suitably an optionally substituted bicyclic heteroaromatic group, preferably an optionally substituted indole, X is O or S, and R2 is H, hydroxy, amino, $C_{1-6}$alkyl, hydroxy$C_{1-6}$alkyl or amino$C_{1-6}$alkyl, and salts and solvates thereof and solvates of such salts.

Preferred embodiments of formula (I) are compounds of formula (II) and (III)

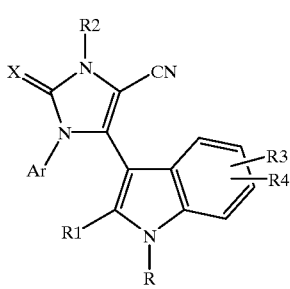

(II)

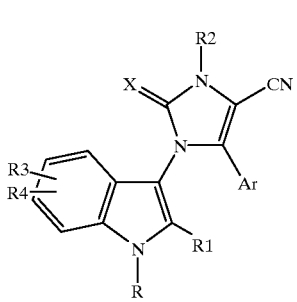

(III)

wherein:
Ar is an optionally substituted aromatic or heteroaromatic group,

X is O or S

R is H, $C_1$alkyl, halo$C_{1-6}$alkyl, bensyl, $C_{1-3}$alkoxy substituted bensyl, nitrile$C_{1-6}$alkyl, hydroxy$C_{1-6}$alkyl, amino$C_{1-6}$alkyl, (pyridinylmethyl)amino$C_{1-6}$alkyl, (mono- or di-$C_{1-6}$alkyl)amino$C_{1-6}$alkyl, (mono- or di-$C_{1-3}$ haloalkyl)amino$C_{1-6}$alkyl, amino$C_{3-7}$cycloalkyl, (mono- or di-$C_{1-6}$alkyl)amino$C_{3-7}$cycloalkyl, (amino$C_{3-7}$cycloalkyl)$C_{1-3}$alkyl, (hydroxy$C_{1-6}$alkyl)amino$C_{1-6}$alkyl, (amino$C_{1-6}$alkyl)amino$C_{1-6}$alkyl, ($C_{1-6}$alkynyl)amino$C_{1-6}$alkyl, (bensyl)amino$C_{1-6}$alkyl, (mono- or di-$C_{1-3}$alkoxy substituted bensyl)amino$C_{1-6}$alkyl, (amino$C_{1-3}$alkylphenyl)

$C_{1-3}$alkyl, (amino$C_{1-3}$alkylthiophenyl)$C_{1-3}$alkyl, (amino$C_{1-3}$alkylpyridinyl)$C_{1-3}$alkyl, guanidino$C_{1-6}$alkyl, (guanidino$C_{1-3}$alkylphenyl)$C_{1-3}$alkyl, amidino$C_{1-6}$alkyl or amidinothio$C_{1-6}$alkyl or a group of the formula

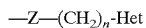

in which

Z is carbonyl or methylene n is an integer of 0–5, and

Het is an optionally substituted 5- or 6-membered heterocyclic group

R1 is H or $C_{1-3}$alkyl

R2 is H, $C_{1-3}$alkyl, hydroxy, amino, hydroxy$C_{1-3}$alkyl or amino$C_{1-3}$alkyl R3 and R4 are each independently H, hydroxy, $C_{1-6}$alkyl, hydroxy$C_{1-6}$alkyl, halo$C_{1-6}$alkyl, $C_{1-3}$alkoxy, carbo$C_{1-6}$ alkoxy, halogen, nitrile, nitro or amino, and salts and solvates thereof and solvates of such salts.

For compounds of formula (II) and (III), the following independent preferences apply:

—Ar is an optionally substituted bicyclic aromatic or an optionally substituted bicyclic heteroaromatic group, —R is amino$C_{1-6}$alkyl, especially aminoethyl, aminopropyl and aminobutyl, (mono- or di-$C_{1-6}$alkyl)amino$C_{1-6}$alkyl, amino$C_{3-7}$cycloalkyl, especially aminocyclopentyl, (mono- or di-$C_{1-6}$alkyl)amino$C_{3-7}$cycloalkyl, (amino$C_{1-3}$alkylphenyl)$C_{1-3}$alkyl, guanidino$C_{1-6}$alkyl, especially guanidinopropyl, amidino$C_{1-6}$alkyl especially amidinobutyl, amidinothio$C_{1-6}$alkyl, especially amidinothiopropyl, or aminomethyl benzyl, —R2 is H, —X is O.

In more preferred embodiments of formula (II) and (III), when Ar is a heteroaromatic or bicyclic heteroaromatic group it includes a single heteroatom selected from N, O and S.

In yet more preferred embodiments of formula (II) and (III), Ar is selected from benzothiophene, naphthyl, optionally substituted phenyl and optionally substituted indolyl. Optional substituents for Ar include alkyl, e.g. methyl, ethyl, propyl, or tert-butyl; alkoxy, e.g. methoxy; aryloxy, e.g. phenoxy; nitro; alkoxycarbonyl, e.g. ethoxycarbonyl; or alkylamino, e.g. propylamino. Preferably alkyl group-containing optional substituents contain 1–6 carbon atoms in each alkyl group.

Preferred compounds according to the present invention include:

5-[1-(3-Aminopropyl)-3-indolyl]-4-cyano-1-(3-indolyl)-2,3-dihydroimidazol-2-one

5-[1-(4-Aminobutyl)-3-indolyl]-4-cyano-1-(3-indolyl)-2,3-dihydroimdazol-2-one

5-[1-(2-Aminoethyl)-3-indolyl]-4-cyano-1-(3-indolyl)-2,3-dihydroimidazol-2-one

5-[1-(3-Aminopropyl)-3-indolyl]-4-cyano-1-(1-methyl-3-indolyl)-2,3-dihydroimidazol-2-one 5-[1-(4-Aminobutyl)-3-indolyl]-4-cyano-1-(1-propyl-3-indolyl)-2,3-dihydroimidazol-2-one 5-[1-(3-Aminopropyl)-3-indolyl]-1-(benzo[b]thiophen-3-yl)-4-cyano-2,3-dihydroimidazol-2-one 5-[1-(3-Amidinothiopropyl)-3-indolyl]-4-cyano-1-(3-indolyl)-2,3-dihydroimidazol-2-one 5-[1-(4-Amidinobutyl)-3-indolyl]-4-cyano-1-(3-indolyl)-2,3-dihydroimidazol-2-one 4-Cyano-5-[1-(3-guanidinopropyl)-3-indolyl]-1-(3-indolyl)-2,3-dihydroimidazol-2-one 5-{1-[3-(Aminomethyl)benzyl]-3-indolyl}-4-cyano-1-(3-indolyl)-2,3-dihydroimidazol-2-one 5-{1-[2-(Aminomethyl)benzyl]-3-indolyl}-4-cyano-1-(1-methyl-3-indolyl)-2,3-dihydroimidazol-2-one 5-{1-[3-(Aminomethyl)benzyl]-3-indolyl}-4-cyano-1-(1-methyl-3-indolyl)-2,3-dihydroimnidazol-2-one 5-{1-[4-(Aminomethyl)benzyl]-3-indolyl}-4-cyano-1-(1-methyl-3-indolyl)-2,3-dihydroimidazol-2-one 5-{1-[6-(Aminomethyl)-2-pyridylmethyl]-3-indolyl}-1-(1-methyl-3-indolyl)-2,3-dihydroimidazol-2-one 5-{1-[5-(Aminomethyl)-2-thiophenylmethyl]-3-indolyl}-4-cyano-1-methyl-3-indolyl)-2,3-dihydroimidazol-2-one 4-Cyano-5-[1-(N,N-dimethylaminopropyl)-3-indolyl]-1-(1-methyl-3-indolyl)-2,3-dihydroimidazol-2-one 5-[1-(4-Aminobutyl)-3-indolyl]-4-cyano-1-(3-nitrophenyl)-2,3-dihydroimidazol-2-one 4-Cyano-5-[1-(N-isopropylamino)propyl)-3-indolyl]-1-(1-methyl-3-indolyl)-2,3-dihydroimidazol-2-one 5-[1-(3-Aminocyclopentyl)-3-indolyl]-4-cyano-(1-methyl-3-indolyl)-2,3-dihihydroimidazol-2-one 4-Cyano-5-[1-(3-hydroxypropyl)-3-indolyl]-1-(3-indolyl)-2,3-dihydroimidazol-2-one 4-Cyano-5-[1-(4-cyanobutyl)-3-indolyl]-1-[1-(ethoxycarbonyl)-3-indolyl]-1,3-dihydroimidazol-2-one 5-[1-(4-Aminobutyl)-3-indolyl]-4-cyano-1-(4-methoxyphenyl)-2,3-dihydroimidazol-2-one 5-[1-(4-Aminobutyl)-3-indolyl]-4-cyano-1-(4-phenoxyphenyl)-2,3-dihydroimidazol-2-one 5-[1-(4-Aminobutyl)-3-indolyl]-1-(4-tert-butylphenyl)-4-cyano-2,3-dihydroimidazol-2-one 5-[1-(4-Aminobutyl)-3-indolyl]-4-cyano-1-[(4-ethoxycarbonyl)phenyl]-2,3-dihydroimidazol-2-one 5-[1-(4-Aminobutyl)-3-indolyl]-4-cyano-1-(1-naphthyl)-2,3-dihydroimidazol-2-one 4-Cyano-5-(3-indolyl)-1-(1-naphthyl)-2,3-dihydroimidazol-2-one 4-Cyano-5-[1-(4-methoxybenzyl)-3-indolyl]-1-(1-methyl-3-indolyl)-2,3-dihydroimidazol-2-one 1-[1-(3-Aminopropyl)-3-indolyl]-4-cyano-5-(1-methyl-3-indolyl)-2,3-dihydroimidazol-2-one 4-Cyano-1-(3-indolyl)-5-(1-methyl-3-indolyl)-2,3-dihydroimidazol-2-one 4-Cyano-1,5-bis-(1-methyl-3-indolyl)-2,3-dihydroimidazol-2-one 5-[1-(4-Aminobutyl)-3-indolyl]-4-cyano-1-(1-methyl-3-indolyl)-2,3-dihydroimidazol-2-one 4-Cyano-5-[1-(3-{methylamino}propyl)-3-indolyl]-1-(1-methyl-3-indolyl)-2,3-dihydroimidazol-2-one 4-Cyano-5-[1-(3-{ethylamino}propyl)-3-indolyl]-1-(1-methyl-3-indolyl)-2,3-dihydroimidazol-2-one 5-[1-(2-Aminomethyl-3-methylbutyl)-3-indolyl]-4-cyano-1-(1-methyl-3-indolyl)-2,3-dihydroimidazol-2-one 4-Cyano-1-(1-methyl-3-indolyl)-5-[1-(3-{1-piperazinyl}propyl)-3-indolyl]-2,3-dihydroimidazol-2-one 4-Cyano-1-(1-methyl-3-indolyl)-5-{1-[3-(4-morpholinyl)propyl]-3-indolyl}-2,3-dihydroimidazol-2-one 4-Cyano-5-{1-[3-(1-imidazolyl)propyl]-3-indolyl}-1-(1-methyl-3-indolyl)-2,3-dihydroimidazol-2-one 5-[1-(3-Bromopropyl)-3-indolyl]-4-cyano-1-(1-methyl-3-indolyl)-2,3 -dihydroimidazol-2-one 5-{1-[3-(2-Aminoethylamino)propyl]-3-indolyl}-4-cyano-1-(1-methyl-3-indolyl)-2,3-dihydroimidazol-2-one 5-{1-[3-({4-Aminobutyl}amino)propyl]-3-indolyl}-4-cyano-1-(1-methyl-3-indolyl)-2,3-dihydroimidazol-2-one 4-Cyano-5-{1-[3-({2-hydroxyethyl}amino)-propyl]-3-indolyl}-1-(1-methyl-3-indolyl)-2,3-dihydroimidazol-2-one 5-{1-[3-[({Benzo[1,3]dioxol-5-yl}methyl)-amino]propyl]-3-indolyl}-4-cyano-1-(1-methyl-3-indolyl)-2,3-dihydroimidazol-2-one 4-Cyano-1-(1-methyl-3-indolyl)-5-[1-[3-({3-propargyl}amino]-propyl)-3-indolyl]-2,3-dihydroimidazol-2-one 4-Cyano-1-(1-methyl-3-indolyl)-5-[1-(3-[{3-pyridyl}methylamino]propyl)-3-indolyl]-2,3-dihydroimidazol-2-one 4-Cyano-5-[1-{3-([2-hydoxyethoxy]ethylamino)propyl}-3-indolyl]-1-(1-methyl-3-indolyl)-3-indolyl]-2,3-dihydroimidazol-2-one 4-Cyano-1-(1-methyl-3-indolyl)-5-[1-(3-(2,2,2-trifluoroethylamino)propyl)-3-indolyl]-2,3-dihydroimidazol-2-one 4-Cyano-5-[1-(3-cyanopropyl)-3-indolyl]-1-(1-methyl-3-indolyl)-2,3-dihydroimidazol-2-one cis-5-[1-(4-Aminocyclohexyl)-3-indolyl]-4-cyano-1-(1-methyl-3-indolyl)-2,3-dihydroimidazol-2-one 5-[1-(4-Aminobutyl)-3-indolyl]-4-cyano-3-methyl-1-(1-propyl-3-indolyl)-2,3-dihydroimidazol-2-one 4-Cyano-5-{1-[3-(guanidinomethyl)benzyl]-3-indolyl}-1-(1-methyl-3-indolyl)-2,3-dihydroimidazol-2-one 4-Cyano-1-(1-methyl-3-indolyl)-5-[1-((2S)-2-pyrrolidine-carbonyl)-3-indolyl]-2,3-dihydroimidazol-2-one 4-Cyano-1-(1-methyl-3-indolyl)-5-[1-((2R)-2-pyrrolidine-carbonyl)-3-indolyl]-2,3-dihydroimidazol-2-one 4-Cyano-1-(1-methyl-3-indolyl)-5-{1-[(1S,3R)-1-(3-toluene-4-sulfonylamino)-cyclopentylmethyl]-3-indolyl}-2,3-dihydroimidazol-2-one 5-{1-[(1S,3R)-1-(3-Amino)cyclopentylmethyl]-3-indolyl}-4-cyano-1-(1-methyl-3-indolyl)-2,3-dihydroimidazol-2-one 4-Cyano-1-(1-methyl-3-indolyl)-5-[1-((2R)-2-pyrrolidinylmethyl)-3-indolyl]-2,3-dihydroimidazol-2-one 4-Cyano-5-[(1S,3S)-1-(3-N,N-dimethylaminocyclopentyl)-3-indolyl]-1-(1-methyl-3-indolyl)-2,3-dihydroimidazol-2-one 5-[1-(4-Aminobutyl)-3-indolyl]-4-cyano-1-(5,6-dichloro-1-methyl-3-indolyl)-2,3-dihydroimidazol-2-one
and salts thereof.

Salts of the compounds of formula (I), (II) and (III) according to the invention are preferably pharmaceutically acceptable salts. Other salts may however be useful in the preparation of the compounds or in the preparation of pharmaceutically acceptable salts.

Pharmaceutically acceptable salts of compounds of the present invention are preferably those well known in the art as being suitable and are preferably acid addition salts and more preferably chloride salts, acetate salts or trifluoroacetate salts.

Solvates of the compounds or salts of the present invention are conveniently hydrates, such as monohydrates or dihydrates.

Compounds of the present invention include all pure stereoisomers and all mixtures thereof.

Preparation of the Compounds of the Invention

Compounds of formula (I) may be synthesized in the following ways:

(A) Compounds of formula (I) may be synthesized by converting a compound of formula (I) to a salt, especially a pharmaceutically acceptable salt thereof, or vice versa; or converting a salt, especially a pharmaceutically acceptable salt of a compound of formula (I) into a different salt, especially a pharmaceutically acceptable salt.

(B) Compounds of formula (I) may be synthesized by dehydration of a compound of formula (IV):

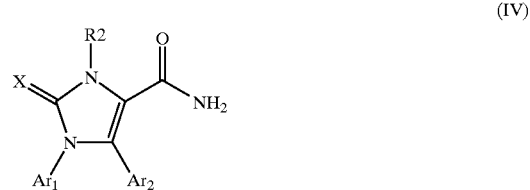

(IV)

in which X, $Ar_1$, $Ar_2$ and R2 are as defined for formula (I).

The dehydration may be conveniently performed in the presence of trimethylsilyl polyphosphate in refluxing dichloromethane.

Compounds of formula (II) may be prepared as shown below. Compounds of formula (III) are prepared in an analogous manner to the methods for the preparation of compounds of formula (II).

Compounds of formula (II) may be synthesised by dehydration of a compound of formula (V):

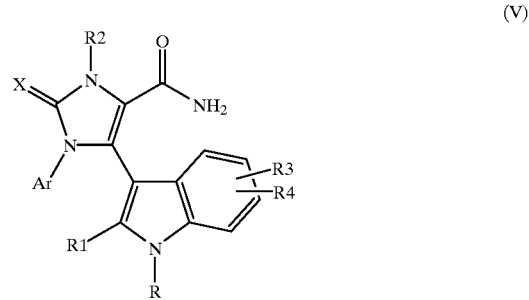

(V)

in which X, Ar, R and R1–R4 are as defined for formula (II).

The dehydration may be conveniently performed as in process (B) above.

Compounds of formula (II) in which Ar, R or R1–R4 carries functional group(s) which might be sensitive to or interfere with the reaction conditions in process (B), can be prepared by dehydration of a corresponding compound of formula (V), but in which the functional groups on Ar, R or R1–R4 are suitably protected, followed by subsequent deprotection.

Functional groups that might be sensitive to or interfere with the reaction conditions in process (B), as well as suitable protecting groups and deprotecting methods, are evident to those skilled in the art.

Compounds of formula (II), in which at least one of R, R2 or Ar carries an amino, or hydroxy group; and salts thereof, may be prepared by deprotecting a compound of formula (VI) corresponding to formula (V) but in which at least one of R, R2 or Ar carries a protected amino or hydroxy group.

In the processes described above, the protecting groups and conditions for deprotection are well known to those skilled in the art. Suitable protecting groups for amino groups are e.g naphthaloyl groups and the deprotecting agent may be methylamine in e.g. water. The deprotecting step may be carried out in a suitable solvent, e.g. tetrahydrofuran at about 10–30° C., e.g for about 5 hours. The hydroxy groups may be protected as their corresponding acetoxy groups and the deprotecting agent may be methylamine in e.g. water. The deprotecting step may be carried out in a suitable solvent, e.g tetrahydrofuran at about 10–30° C., e.g for about 16 hours.

The starting materials for the above processes (A) and (B) may be made by the methods described herein and particularly by those methods set out in the Examples or by methods analogous thereto. Other conventional methods for making the starting materials will be evident to those skilled in the art.

Compounds of formula (V) may be synthesized by intramolecular condensation of a compound of formula (VII):

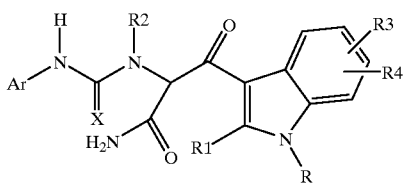

(VII)

in which X, Ar, R and R1–R4 are as defined for formula (II).

The intramolecular condensation may be performed under acidic conditions, preferably in acetic acid at 110° C., or in the presence of scandium(III)trifluoromethane sulfonate in methanol at 105° C.

Compounds of formula (VII) in which R is not H may be synthesized by alkylation, with an optionally substituted alkylating agent, of compounds of formula (VIII):

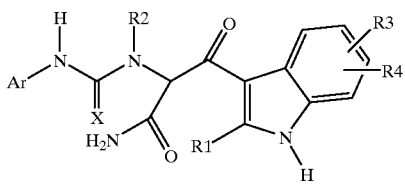

(VIII)

in which X, Ar and R1–R4 are as defined for formula (II).

The alkylating agent may be an alkyl halide, or an alkylating agent carrying a protected amino or hydroxy group. Functional groups on compounds of formula (VIII) that might be sensitive for the alkylating conditions are suitably protected.

When Ar is indolyl in the alkylation of compounds of formula (VIII), the indolyl nitrogen may be protected preferably with an ethoxy carbonyl group.

Compounds of formula (VIII) may be prepared by reaction of the appropriate isocyanate or thioisocyanate with a corresponding 2-amino-3-(3-indolyl)-3-oxopropionamide by standard techniques.

Compounds of formula (II) in which R2 is H, X is O and Ar is indolyl substituted on the indole nitrogen with an alkyl group, and in which R is an alkyl carrying an amino or hydroxy group, may be prepared by deprotecting a compound of formula (IX) in which R' represents an alkyl group, R" represents H or OMe, R is alkyl carrying a protected amino or hydroxy group and R1, R3 and R4 are as defined for formula (II).

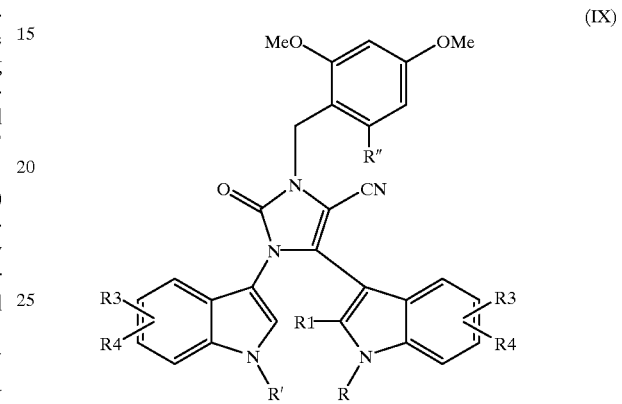

(IX)

Deprotection of the 2,4-dimethoxybenzyl or 2,4,6-trimethoxybenzyl group may be carried out in the presence of trifluoromethane sulfonic acid or trimethylsilyl bromide in refluxing acetonitrile.

Protecting groups and conditions for the deprotection for the amino and hydroxy groups may be similar to those described above.

Compounds of formula (IX) may be prepared, by alkylation with an alkylating agent preferably in the presence of a base, of compounds of formula (X):

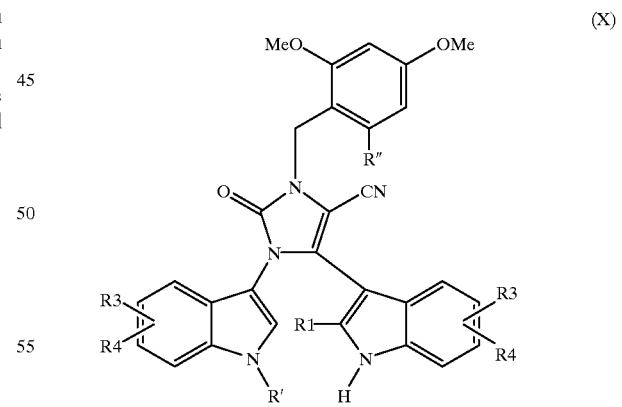

(X)

in which R' is an alkyl group, R" is H or OMe, and R1, R3 and R4 are as defined in formula (II).

The alkylating agent may be an alkyl halide carrying a protected amino or hydroxy group, and the preferred conditions are potassium or cesium carbonate in N,N-dimethyl formamide.

Compounds of formula (X) may be synthesized by dehydration of compounds of formula (XI):

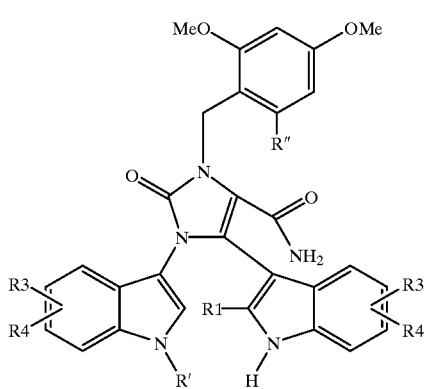

in which R' is an alkyl group, R" is H or OMe, and R1, R3 and R4 are as defined in formula (II).

Compounds of formula (XI) may be synthesized by intramolecular condensation of compounds of formula (XII):

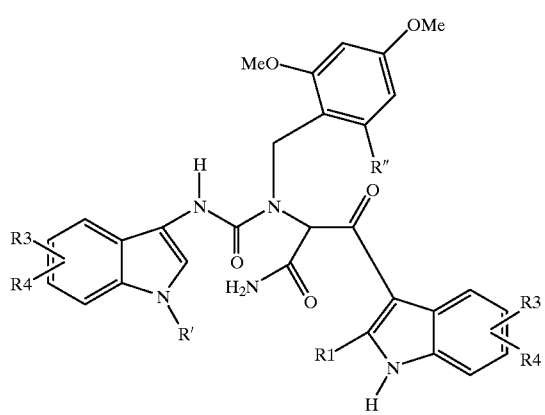

in which R' is an alkyl group and R" is H or OMe, and R1, R3 and R4 are as defined in formula (II).

Compounds of formula (XII) may be prepared by reaction of the appropriate isocyanate with a corresponding amino ketone.

The reaction conditions for making the starting materials, compounds of formula (X), (XI) and (XII), are similar to those described for the analogous transformations in process (B).

Compounds of formula (II) in which X is O and Ar is indolyl substituted on the indole nitrogen with an alkyl group and in which R is an alkyl carrying a thioamidino, monoalkyl amino or diallyl amino may be prepared by reacting a compound of formula (XIII) with thiourea, or a suitable monoalkyl or dialkyl amine:

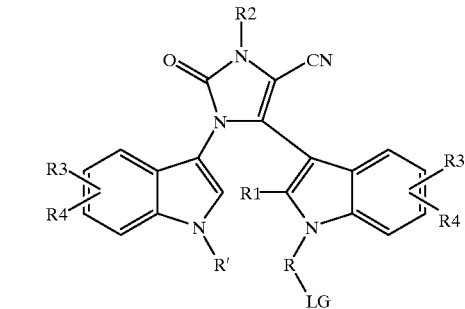

in which R1–R4 are as defined for formula (II), R' and R are alkyl groups and LG is a leaving group, e.g. mesylate.

Compounds of formula (XIII) may be synthesized by transforming under standard conditions, the alcohol function in compounds of formula (XIV) to leaving groups:

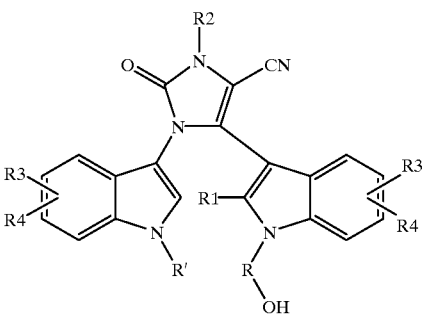

in which R1–R4 are as defined for formula (I), and R' and R are alkyl groups.

Compounds of formula (II) in which Ar is indolyl and R is alkyl carrying an amidino or a guanidino group may be synthesized using standard methods, from compounds of formula (XV) corresponding to formula (II) but in which Ar is indolyl, if necessary protected on the indole nitrogen e.g. with an ethoxy carbonyl, and R is alkyl carrying a nitrile or primary amine, respectively, by reacting with hydrogen chloride in ethanol followed by ammonia in methanol or by reacting with 3,5-dimethylpyrazole-1-carboxamidinium nitrate in refluxing ethanol and in the presence of a base, respectively.

Compounds of formula (II) in which X is O, R2 is H, R is alkyl and Ar is indolyl substituted on the indole nitrogen with an alkyl carrying an amino group, may be prepared by deprotecting a compound of formula (XVI) in which R' is an alkyl carrying a protected amino group and R is an alkyl group:

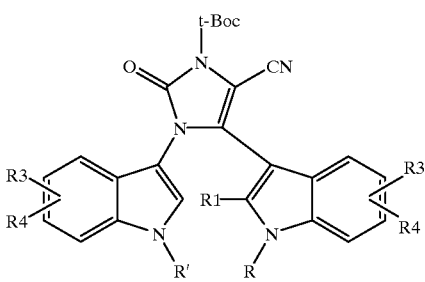

where t-Boc is a t-butoxycarbonyl group, and R1, R3 and R4 are as defined for formula (II).

The protecting groups and conditions for deprotection are similar to those mentioned earlier.

Compounds of formula (XVI) may be prepared by selective removal of a Troc group from a compound of formula (XVII):

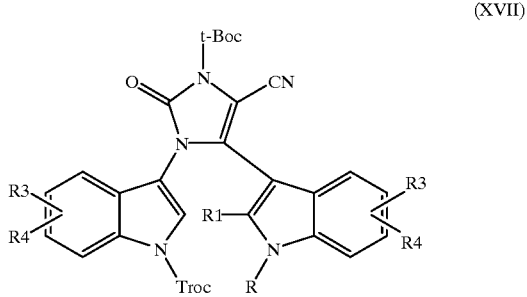

(XVII)

in which R is alkyl, R1, R3 and R4 are as defined for formula (II), and Troc is a 2,2,2-trichloroethoxy carbonyl group, followed by subsequent alkylation under standard conditions, with an alkyl carrying a protected amino group. Selective deprotection of the Troc group is carried out with cadmium in acetic acid and N,N-dimethyl formamide (DMF).

Compounds of formula (XVII) may be prepared by introducing a t-Boc group, under standard conditions, to compounds of formula (II) but in which X is O and the Ar group is a Troc protected indolyl, R2 is H and R is alkyl.

Persons skilled in the art will appreciate that, in order to obtain compounds of the invention in an alternative, and, on some occasions, more convenient, manner, the individual process steps mentioned herein may be performed in a different order, and/or the individual reactions may be performed at a different stage in the overall route. This will e.g. on factors such as the nature of other functional groups present in a particular substrate, the availability of key intermediates and the protecting group strategy (if any) to be adopted.

Prodrugs and Intermediates

It will also be appreciated by those skilled in the art that, although certain protected derivatives of compounds of formula (I), which may be made prior to a final deprotection stage, may not possess pharmacological activity as such, they may be administered parenterally or orally and thereafter metabolized in the body to form compounds of the invention which are pharmacologically active. Such derivatives may therefore be described as "prodrugs". Moreover, certain compounds of formula (I) may act as prodrugs of other compounds of formula (I).

All prodrugs of compounds of formula (I), (II) and (III) are included within the scope of the present invention.

Novel intermediates as described hereinbefore and their use in the manufacture of other compounds of the present invention also form part of the invention. Thus, according to a further aspect of the invention there is provided compounds of formulae (VII) to (XVII) as defined hereinbefore, or protected derivatives of any of these compounds.

Medical and Pharmaceutical Use

Also provided according to the present invention are compounds of the present invention for use in medical therapy; the use of compounds of the present invention in the manufacture of medicaments for use in medical therapy, and more particularly in the treatment of the conditions described herein; and methods of medical therapy comprising the administration of a therapeutically effective amount of a compound of the present invention to an individual requiring such therapy.

The term 'medical therapy' as used herein is intended to include prophylactic, diagnostic and therapeutic regimens carried out in vivo or ex vivo on humans or other mammals The compounds of formula (I), (II) and (III) and salts, especially pharmaceutically acceptable salts, and solvates thereof, and solvates of such salts, are useful because they demonstrate pharmacological activity. In particular they demonstrate activity as kinase inhibitors, especially PKC inhibitors, e.g. as is shown by their activity in the in vitro assays described in Granet, R. A. et al, Analyt. Biochem. 1987; 163, 458–463; Olsson, H. et al, Cell Signal 1989, 1, 405–410; and Chakravarthy, B. R. et al, Analyt. Biochem. 1991, 196, 144–150.

The compounds of the invention are indicated for use in the treatment of inflammatory, immunological, bronchopulmonary, cardiovascular, oncological or CNS-degenerative disorders; preferably for oral or topical treatment of inflammatory and/or immunological disorders, such as the oral or topical treatment of airway diseases involving inflammatory conditions, e.g. asthma, bronchitis; or atopic diseases, e.g. rhinitis or atopic dermatitis; inflammatory bowel diseases, e.g. Crohn's disease or colitis; autoimmune diseases e.g. multiple sclerosis, diabetes, atherosclerosis, psoriasis, systemic lupus erythematosus or rheumatoid arthritis; malignant diseases, e.g. skin or lung cancer; HIV infections or AIDS; or for inhibiting rejection of organs/transplants. The compounds of the invention are also indicated for use in treatment of heart failure, and in treatment of diabetic patients with macular edema or diabetic retinopathy.

Pharmaceutical Preparations

The dose of the compound to be administered will depend on the relevant indication, the age, weight and sex of the patient and may be determined by a physician. The dosage will preferably be in the range of from 0.01 mg/kg to 10 mg/kg.

The compounds may be administered topically, e.g. to the lung and/or the airways, in the form of solutions, suspensions, HFA aerosols or dry powder formulations, e.g. formulations in the inhaler device known as the Turbuhaler®; or systemically, e.g. by oral administration in the form of tablets, pills, capsules, syrups, powders or granules, or by parenteral administration, e.g. in the form of sterile parenteral solutions or suspensions, or by rectal administration, e.g. in the form of suppositories.

The compounds of the invention may be administered on their own or as a pharmaceutical composition comprising the compound of the invention in combination with a pharmaceutically acceptable diluent, adjuvant and/or carrier. Particularly preferred are compositions not containing material capable of causing an adverse, e.g. an allergic, reaction.

Dry powder formulations and pressurized HFA aerosols of the compounds of the invention may be administered by oral or nasal inhalation. For inhalation the compound is desirably finely divided. The finely divided compound preferably has a mass median diameter of less than 10 μm, and may be suspended in a propellant mixture with the assistance of a dispersant, such as a $C_8$–$C_{20}$ fatty acid or salt thereof, (e.g. oleic acid), a bile salt, a phospholipid, an alkyl saccharide, a perfluorinated or polyethoxylated surfactant, or other pharmaceutically acceptable dispersant.

The compounds of the invention may also be administered by means of a dry powder inhaler. The inhaler may be a single or a multi dose inhaler, and may be a breath actuated dry powder inhaler.

One possibility is to mix the finely divided compound with a carrier substance, e.g. a mono-, di- or polysaccharide, a sugar alcohol, or another polyol. Suitable carriers are sugars, e.g. lactose, glucose, raffinose, melezitose, lactitol, maltitol, trehalose, sucrose, mannitol; and starch. Alternatively the finely divided compound may be coated by another substance. The powder mixture may also be dispensed into hard gelatin capsules, each containing the desired dose of the active compound.

Another possibility is to process the finely divided powder into spheres which break up during the inhalation procedure. This spheronized powder may be filled into the drug reservoir of a multidose inhaler, e.g. that known as the Turbuhaler® in which a dosing unit meters the desired dose which is then inhaled by the patient. With this system the active compound, with or without a carrier substance, is delivered to the patient.

For oral administration the active compound may be admixed with an adjuvant or a carrier, e.g. lactose, saccharose, sorbitol, mannitol; a starch, e.g. potato starch, corn starch or amylopectin; a cellulose derivative; a binder, e.g. gelatin or polyvinylpyrrolidone, and/or a lubricant, e.g. magnesium stearate, calcium stearate, polyethylene glycol, a wax, paraffin, and the like, and then compressed into tablets. If coated tablets are required, the cores, prepared as described above, may be coated with a concentrated sugar solution which may contain e.g. gum arabic, gelatin, talcum, titanium dioxide, and the like. Alternatively, the tablet may be coated with a suitable polymer dissolved in a readily volatile organic solvent.

For the preparation of soft gelatin capsules, the compound may be admixed with e.g. a vegetable oil or polyethylene glycol. Hard gelatin capsules may contain granules of the compound using either the above mentioned excipients for tablets. Also liquid or semisolid formulations of the drug may be filled into hard gelatin capsules.

Liquid preparations for oral application may be in the form of syrups or suspensions, for example solutions containing the compound, the balance being sugar and a mixture of ethanol, water, glycerol and propylene glycol. Optionally such liquid preparations may contain coloring agents, flavoring agents, saccharine and/or carboxymethylcellulose as a thickening agent or other excipients known to those skilled in art.

The compounds of the invention may also be administered in conjunction with other compounds used for the treatment of the above conditions.

EXAMPLES

The following Examples are intended to illustrate, but in no way limit the scope of the invention.

GENERAL METHODS

All reactions were performed in dried glassware in an argon atmosphere at room temperature, unless otherwise noted. Tetrahydrofuran (THF) was distilled from sodium benzophenone ketyl under $N_2$ prior to use. N,N-Dimethyl formamide (DMF) was distilled from calcium hydride and stored over molecular sieves. All other solvents and reagents and solvents were used as received.

Chromatography, unless otherwise stated, was carried out using a Chromatotron® (a centrifugally accelerated, radial preparative chromatography, the plates used were prepared using Merck Silica Gel $PF_{254}$ containing gypsum.

$^1$H-NMR spectra were recorded on a Varian Inova-400 or Unity-500+ instrument. The central solvent peak of chloroform-$d_6$ ($\delta_H$ 7.27 ppm), dimethylsulfoxide-$d_6$ ($\delta_H$ 2.50 ppm) or methanol-$d_4$ ($\delta_H$ 3.35 ppm) were used as internal references. Low-resolution mass spectra were recorded on an Autospec-Q, Fisons Analytical, double focusing sector instrument equipped with a LSIMS interface. Low resolution mass spectra were also obtained on a Hewlett Packard 1 100 LC-MS system equipped with an APCI ionization chamber.

Example 1

5-[1-(3-Aminopropyl)-3-indolyl]-4-cyano-1-(3-indolyl)-2,3-dihydroimidazol-2-one trifluoroacetic acid salt a) [1-Carbamoyl-2-(3-indolyl)-ethyl]-carbamic acid benzyl ester To a solution of 8.35 g (0.21 mol) NaOH in 100 ml of water was added 200 ml of THF followed by 25.0 g (0.104 mol) of L-tryptophanamide hydrochloride. The mixture was cooled on ice and 19.6 g (0.114 mol) of benzylchloroformate was added under vigorous stirring during 5 minutes. The ice bath was removed and the mixture was stirred for 1 hour.

The mixture was partitioned between 150 ml of water and 250 ml of EtOAC. The organic phase was collected and the aqueous phase extracted with an additional 100 ml of EtOAc. The combined organic phases were washed with water and brine. After evaporation the solid obtained was suspended in 400 ml of diethyl ether and filtered, the sub-title product, 34.0 g (97%), was obtained as a white solid.

$^1$H-NMR (300 MHz, DMSO-$d_6$): δ 2.83–2.97 (1H, m), 3.06–3.16 (1H, m), 3.35 (1H, s), 4.22 (1H, dt, J 9.3 4.2 Hz), 4.95 (2H, s), 6.97 (1H, t, J 6.7 Hz), 7.01–7.17 (3H, m), 7.20–7.37 (6H, m), 7.49 (1H, s), 7.64(1H, d, J 7.9 Hz), 10.81 (1H, s)

FAB-MS: m/z 338.1 [MH+]

b) [1-Carbamoyl-2-(3-indolyl)-2-oxoethyl]arbamic acid benzyl ester

To a solution of the product of step a) 2.50 g (7.41 mmol) in 90 ml of THF and 10 ml of water was added 3.35 g (14.7 mmol) of DDQ, and the mixture was stirred for 2.5 hours under nitrogen.

The solvent was evaporated and the residue dissolved in 200 ml of EtOAc. Extraction with 1M NaOH (3×50 ml), followed by evaporation of the organic phase gave a dark viscous oil. After addition of minimum amounts of methanol, the sub-title product immediately started to precipitate. Cooling for 30 minutes and followed by filtration gave 1.05 g (40%) of the sub-title product.

FAB-MS m/z: 352.0 [MH+]

c) 2-Amino-3-(3-indolyl)-3-oxopropionamide acetic acid salt

To a solution of the product of step b) 0.51 g (1.45 mmol) in 10 ml of EtOAc and 10 ml of glacial acetic acid was added 0.2 g 5% Pd(C). Hydrogenation for 2 hours followed by removal of the catalyst by filtration through celite. The filtrate was evaporated, and the residue co-evaporated with methanol/toluene, and then with $CH_2Cl_2$. The crude sub-title product was used in the next step with no further purification.

APCI-MS: m /z 218.0 [MH+]

d) 3-{3-[1-Carbamoyl-2-(3-indolyl)-2-oxoethyl]-ureido}-1-(ethoxycarbonyl)-indole A solution of 1.10 g (4.27 mmol) of 3-azidocarbonyl-indole-1-carboxylic acid ethyl ester (Suvorov et al. *Khimiya Gereotsiklicheskikh Soedinenii*, 8 (1975) 1099–1105) in 15 ml of absolute benzene was heated reflux for 6 hours under nitrogen. After cooling to room temperature the benzene solution was rapidly added to a freshly prepared suspension of 2.04 g (4.27 mmol) of the product of step c) and 0.55 g (4.27 mmol) of ethyldiisopropylamine in 20 ml of THF.

The resulting solution was stirred for 2 hours. The solvents were evaporated and the residue suspended in 25 ml of water and stirred for 10 minutes. The product was filtered, washed with 2×20 ml of water and finally dried in air, giving 1.64 g (86%) of the sub-title compound as a yellowish solid.

$^1$H-NMR (500 MHz, DMSO-$d_6$): δ 1.37 (3H, t, J 7.4 Hz), 4.40 (2H, q, J 6.7 Hz), 5.64 (1H, d, J 8.1 Hz), 7.16–7.28 (3H, m), 7.30–7.42 (3H, m), 7.51 (1H, dd, J 7.1, 2.6 Hz), 7.70 (1H, d, J 7.7 Hz), 7.80 (1H, s), 7.83 (1H, bs), 8.10 (1H, d, J 8.4 Hz), 8.18 (1H, dd, J 6.1, 1.9 Hz), 8.68 (1H, s), 9.27 (1H, s), 12.18 (1H, s).

FAB-MS: m/z 448.1 [MH+].

e) 3-[3-(1-Carbamoyl-2-{1-[3-(1,3-dioxo-1,3-dihydroisoindol-2-yl)-propyl]-3-indolyl}-2-oxoethyl)-ureido]-1-(ethoxycarbonyl)-indole A solution of 0.10 g (0.223 mmol) of the product from step d), 0.15 g (0.56 mmol) of N-(3-bromopropyl) phthalimide, 0.10 g (0.72 mmol) of $K_2CO_3$ and 1.5 ml of DMF. The flask was sealed and heated to 65° C. for 5 hours. The reaction mixture was partitioned between 10 ml of EtOAc and 10 ml of water. The organic phase was collected and the aqueous phase was extracted with an additional 10 ml of EtOAc. The combined organic phases were washed with water and brine. The organic phase was evaporated to give a yellowish solid. The solid was suspended in 20 ml of diethyl ether and stirred for 30 minutes. The precipitate was allowed to settle and the ethereal phase was removed. The residual precipitate was dried in vacuum to give 100 mg (70%) of the sub-title product.

$^1$H-NMR (500 MHz, DMSO-$d_6$): δ 1.36 (3H, t, J 7.0 Hz), 2.16 (2H, p, J 7.0 Hz), 3.58–3.72 (2H, m), 4.33–4.44 (4H, m), 5.58 (1H,d, J 7.6 Hz), 7.20–7.34 (5H, m), 7.38 (1H, s), 7.66 (2H, d, J 7.8 Hz), 7.72 (1H, s), 7.76 (1H, s), 7.81 (4H, s), 8.00 (1H, d, J 7.8 Hz), 8.19 (1H, d, J 7.8 Hz), 8.76 (1H, s), 9.24 (1H, s)

FAB-MS: m/z 635.0 [MH+]

f) 4-Carbamoyl-5-{1-[3-(1,3-dioxo-1,3-dihydroisoindol-2-yl)-propyl]-3-indolyl}-1-[1-(ethoxycarbonyl)-3-indolyl]-1,3-dihydroimidazol-2-one A solution of 0.10 g (0.16 mmol) of the product of step e) in 10 ml of glacial acetic acid was heated with stirring on an oil bath at 110° C. overnight.

After cooling the acetic acid was evaporated. Residual amounts of AcOH was removed by dissolving the residue in $CH_2Cl_2$ and co-evaporating with toluene, to give 0.10 g of the sub-title compound.

FAB-MS: m/z 617.1 [MH+]

g) 4-Cyano-5-{1-[3-(1,3-dioxo-1,3-dihydroisoindol-2-yl)-propyl]-3-indolyl}-1-[1-(ethoxycarbonyl)-3-indolyl]-1,3-dihydroimidazol-2-one To 0.10 g (0.16 mmol) of the product of step f) was added 10 ml of a solution of TMS-polyphosphate (Yokoyama et al. *Synthesis* (1982) 591–592) in $CH_2Cl_2$. The flask was sealed and heated on an oil bath to 50° C. for 3 hours. The organic phase was diluted to 20 ml with $CH_2Cl_2$ and then washed with 10 ml of water, 5 ml of 1M sulfuric acid and finally with 5 ml of brine. The organic phase was evaporated, and the residue was purified by chromatography on silica ($CH_2Cl_2$:MeOH 97:3), furnishing 65 mg (67%) of the sub-title product.

$^1$H-NMR (500 MHz, CDCl$_3$): δ 1.41 (3H, t, J 6.7 Hz), 1.90 (2H, p, J 6.4 Hz), 3.01 (2H, t, J 6.4 Hz), 4.00 (2H, t, J 6.4 Hz), 4.40 (2H, q, J 7.1 Hz), 7.03 (1H, t, J 7.5 Hz), 7,10 (1H, d, J 7.9 Hz), 7.14–7.24 (2H, m), 7.26 (2H, s), 7.38 (1H, s), 7.69 (1H, d, J 7.7 Hz), 7.75–7.80 (2H, m), 7.84–7.88 (2H, m), 7.91 (1H, s), 8.00 (1H, d, J 8.1 Hz), 8.77 (1H, s)

FAB-MS: m/z 599.1 [MH+]

To the 65 mg (0.11 mmol) of product of step f) was added 15 ml of THF and 6 ml of aqueous methylamine (40%), and the mixture was stirred for 2.5 hours. Removal of the solvent gave a semi-crystalline material. The compound was purified by chromatography on silica ($CH_2Cl_2$:MeOH 90:10 to remove rest the impurities and MeOH:TEA 95:5 to elute the product), to give 30 mg (76%) of the free amine. The amine was treated with 1% TFA in water followed by lyophilization to give the title product.

$^1$H-NMR (500 MHz, DMSO-$d_6$): δ 1.87 (2H, p, J 7.4 Hz), 2.55–2.62 (2H, m), 4.17 (2H, t, J 7.1 Hz), 6.89 (1H, t, J 7.3 Hz), 6.97 (1H, t, J 7.3 Hz), 7.04 (1H, t, J 7.3 Hz), 7.10–7.15 (2H, m), 7.32 (1H, d, J 8.4 Hz), 7.38 (1H, d, J 8.2 Hz), 7.46 (1H, s), 7.48 (1H, s), 7.50 (1H, d, J 2.7 Hz), 7.62 (3H, bs), 11.24 (1H, s), 11.39 (1H, s)

FAB-MS: m/z 397.1 [MH+]

Example 2

5-[1-(3-Aminopropyl)-3-indolyl]-1-(benzo[b]thiophen-3-yl)-4-cyano-2,3-dihydroimidazol-2-one acetic acid salt The title product was prepared according to the procedure of Example 1, starting from benzo[b]thiophene-3-carbonyl azide [Galvez, C et al. *Synthesis* (1983) 932–933].

$^1$H-NMR (500 MHz, DMSO-$d_6$): d 1.02 (2H, p, J 8.4 Hz), 1.53 (2H, p, J 8.2 Hz), 2.42–2.46 (2H, m), 4.03 (2H, t, J 7.2 Hz), 6.95 (2H, t, J 7.8 Hz), 7.10 (2H, t, J 8.0 Hz), 7.20–7.34 (3H, m), 7.35–7.45 (3H, m), 7.85–7.95 (2H, m)

Example 3

4-Cyano-5-[1-(3-hydroxypropyl)-3-indolyl]-1-(3-indolyl)-2,3-dihydroimidazol-2-one a) 3-(3-{2-[1-(3-Acetoxypropyl)-3-indolyl]-1-carbamoyl-2-oxoethyl}-ureido)-indole-1-carboxylic acid ethyl ester To 0.25 g (0.56 mmole) of the product of Example 1d) in 2 ml of DMF was added 0.17 g (0.94 mmole) of 3-bromopropyl acetate and, 0.25 g (1.8 mmole) of $K_2CO_3$. After heating to 50° C. over night the mixture was distributed between 15 ml of EtOAc and 15 ml of water. The aqueous phase was extracted with an additional 10 ml of EtOAc. The combined organic phases were washed with water and brine and evaporated to give a crude, which was purified on silica ($CH_2Cl_2$:MeOH 95:5) to give 0.19 g (63%) of the sub-title compound.

$^1$H-NMR (400 MHz, DMSO-$d_6$): δ 1.34 (3H, t, J 7.2 Hz), 1.93 (3H, s), 2.16 (2H, p, J 7.0 Hz), 4.01 (2H, t, J 6.2 Hz), 4.32–4.41 (4H, m), 5.61 (1H, d, J 7.8 Hz), 7.15–7.40 (6H, m), 7.63 (1H, d, J 7.8 Hz), 7.68 (1H, d, J 7.8 Hz), 7.73–7.79 (2H, m), 8.07 (1H, d, J 7.8 Hz), 8.18 (1H, d, J 7.4 Hz), 8.74 (1H, s), 9.26 (1H, s)

FAB-MS m/z: 548.1 [MH+]

b) 5-[1-(3-Acetoxypropyl)-3-indolyl]-4-carbamoyl-1-[1-(ethoxycarbonyl)-3-indolyl]-1,3-dihydroimidazol-2-one A solution of 0.19 g (0.35 mmole) of the product of step a) in 20 ml of glacial acetic acid was heated to 115° C. over night and then allowed to cool. The solvent was evaporated and the residue was co-evaporated with toluene, to give 0.17 g (93%) of the sub-title compound.

FAB-MS m/z: 530.1 [MH+]

c) 5-[1-(3-Acetoxypropyl)-3-indolyl]-4-cyano-1-[1-(ethoxycarbonyl)-3-indolyl]-1,3-dihydroimidazol-2-one A solution of 0.14 g (0.26 mmole) of the product of step b) in 7 ml of TMS-polyphosphate was heated to 50° C. for 4 hours. The mixture was diluted to 20 ml with $CH_2Cl_2$ and washed with water and brine. The organic phase was and evaporated and the residue purified by chromatography on silica ($CH_2Cl_2$:MeOH 98:2), to give 0.11 g (82%) of the sub-title compound.

$^1$H-NMR (400 MHz, in $CDCl_3$): δ 1.47 (3H, t, J 7.1 Hz), 1.88 (2H, p, J 6.3 Hz), 2.01 (3H, s), 3.67 (2H, t, J 5.8 Hz), 4.08 (2H, t, J 6.4 Hz), 4.50 (2H, q, J 7.2 Hz), 7.02 (1H, s), 7.10–7.34 (6H, m), 7.61 (1H, d, J 8.6 Hz), 7.80 (1H, s), 8.18 (1H, d, J 8.1 Hz), 9.35 (1H, s)

FAB-MS m/z: 512.1 [MH+]

In a flask was dissolved 0.11 g (0.21 mmole) of the product from c), in 20 ml of THF and 10 ml of aqueous methylamine (40%) was added. The flask was sealed and stirred over night, whereafter the solvent was evaporated to give 86 mg of the title compound.

FAB-MS: m/z 398.1 [MH+]

Example 4

5-[1-(3-Amidinothiopropyl)-3-indolyl]-4-cyano-1-(3-indolyl)-2,3dihydroimidazol-2-one trifluoroacetic acid salt a) 3-{3-[5-Cyano-3-(3-indolyl)-2-oxo-2,3-dihydro-1H-imidazol-4-yl]-1-indolyl}-propyl methanesulfonate To a solution of 85 mg (0.22 mmol) of the title compound in Example 3 in 15 ml of pyridine was methanesulfonic acid anhydride 75 mg (0.43 mmol) added. The reaction was stirred overnight at room temperature. The pyridine was removed in vacuum and the residue was purified by chromatography on silica ($CH_2Cl_2$:MeOH 95:5), furnishing 49 mg (50%) of the sub-title product.

$^1$H-NMR (400 MHz, $CD_3OD$): δ 1.85 (2H, p, J 6.1 Hz), 2.75 (3H, s), 3.61 (2H, t, J 5.7 Hz), 4.08 (2H, t, J 6.4 Hz), 6.88 (1H, t, J 7.7 Hz), 7.00–7.19 (5H, m), 7.30–7.38 (3H, m), 7.50 (1H, d, J 7.9 Hz), 8.53 (1H, d, J 5.1 Hz), 10.84 (1H, s)

FAB-MS: m/z 476.1 [MH+]

A solution of 46 mg (0.10 mmol) of the product of step a), and 30 mg (0.4 mmol) of thiourea in 25 ml of absolute ethanol was heated to 90° C. overnight. The solvent was evaporated and the residue was purified by chromatography on silica ($CH_2Cl_2$:MeOH: TEA), giving a crude product, which was further purified by preparative HPLC (C18-reversed phase, acetonitrile-water trifluoroacetic acid). The title compound was obtained after lyophilization, giving 25 mg (44%) as a white solid.

$^1$H-NMR (400 MHz, DMSO-$d_6$): δ 1.83 (2H, p, J 7.2 Hz), 2.74 (2H, t, J 7.7 Hz), 4.14 (2H, t, J 6.9 Hz), 6.85 (1H, t, J 7.5 Hz), 6.97–7.10 (3H, m), 7.14 (1H, t, J 8.1 Hz), 7.30–7.36 (2H, m), 7.42–7.47 (2H, m), 5.53 (1H, d, J 2.7 Hz), 9.06 (4H, s), 11.29 (1H, s), 11.39 (1H, s)

FAB-MS: m/z 456.0 [MH+]

Example 5

4-Cyano-5-[1-(4-cyanobutyl)-3-indolyl]-1-[1-(ethoxycarbonyl)-3-indolyl]-1,3-dihydroimidazol-2-one The title product was prepared according to the procedure of Example 1 step d)–g) starting from 5-bromo-pentanenitrile.

$^1$H-NMR (400 MHz, $CDCl_3$): δ 1.08 (2H, p, J 7.2 Hz), 1.48 (3H, t, J 7.1 Hz), 1.74 (2H, p, J 7.1 Hz), 2.11 (2H, t, J 7.1 Hz), 4.05 (2H, t, J 6.5 Hz), 4.51 (2H, q, J 7.0 Hz), 6.92 (1H, s), 7.10–7.23 (3H, m), 7.26 (2H, bs), 7.33 (1H, t, J 8.0 Hz), 7.63 (1H, d, J 8.4 Hz), 7.85 (1H, s), 8.20 (1H, d, J 8.4 Hz), 9.81 (1H, s)

FAB-MS: m/z 493.2 [MH+]

Example 6

5-[1-(4-Amidinobutyl)-3-indolyl]-4-cyano-1-(3-indolyl)-2,3-dihydroimidazol-2-one trifluoroacetic acid salt A portion of 90 mg (0.18 mmol) of the product obtained in Example 5 was dissolved in 15 ml of absolute ethanol saturated with HCl. The mixture was stirred at room temperature for 2 days. The solvent was evaporated, and the residue diluted with methanol saturated with $NH_3$. The mixture was stirred overnight at room temperature. The solvent was evaporated and the residue purified by preparative HPLC (C18-reversed phase, acetonitrile-water trifluoroacetic acid). The title compound was obtained after lyophilization, giving 40 mg (40%) as a white solid.

$^1$H-NMR (500 MHz, DMSO-$d_6$): δ 1.31 (2H, p, J 7.9 Hz), 1.55 (2H, p, J 7.4 Hz), 2.27 (2H, t, J 7.8 Hz), 4.09 (2H, t, J 7.3 Hz), 6.87 (1H, t, J 7.7 Hz), 6.98 (1H, t, J 7.7 Hz), 7.02–7.07 (1H, m), 7.09–7.15 (2H, m), 7.33 (1H, d, J 8.4 Hz), 7.40 (1H, s), 7.39–7.45 (2H, m), 7.51 (1H, d, J 2.66 Hz), 8.49 (2H, s), 8.84 (2H, s), 11.22 (1H, s), 11.37 (1H, s)

FAB-MS: m/z 438.1 [MH+]

Example 7

4-Cyano 5-[1-(3-guanidinopropyl)-3-indolyl]-1-(3-indolyl)-2,3-dihydroimidazol-2-one trifluoroacetic acid salt A mixture of 18 mg (0.045 mmol) of the title compound of Example 1), 18 mg (0.09 mmol) of 3,5-dimethylpyrazol-1-carboxamidine nitrate, and 15 mg of $NaHCO_3$ was dissolved in 15 ml of absolute ethanol. The flask was sealed, heated to 80° C. for 48 hours. The solvent was evaporated, and the residue purified by preparative HPLC (C18-reversed phase, acetonitrile-water trifluoroacetic acid). The title compound was obtained after lyophilization, giving 18 mg (72%) as a white solid.

$^1$H-NMR (500 MHz, DMSO-$d_6$): δ 1.74 (2H, p, J 7.2 Hz), 2.88 (2H, q, J 6.7 Hz), 4.09 (2H, t, J 7.1 Hz), 6.88 (1H, t, J 7.9 Hz), 6.98 (1H, t, J 7.9 Hz), 7.03 (1H, t, J 7.5 Hz), 7.10–7.15 (2H, m), 7.31 (1H, d, J 8.4 Hz), 7.38–7.41 (2H, m), 7.44 (1H, d, J 8.4 Hz), 7.46–7.50 (1H, m), 7.50 (1H, d, J 2.9 Hz), 11.26 (1H, s), 11.38 (1H, s)

FAB-MS: m/z 439.3 [MH+].

Example 8

5-{1-[3-(Aminomethyl)benzyl]-3-indolyl}-4-cyano-1-(3-indolyl)-2,3-dihydroimidazol-2-one trifluoroacetic acid salt The title product was prepared according to the procedure of Example 1, starting from 2-(3-bromomethylbenzyl)-isoindole-1,3-dione.

$^1$H-NMR (500 MHz, DMSO-$d_6$): δ 3.79 (2H, s), 5.29 (2H, s), 6.53 (1H, d, J 8.0 Hz), 6.89 (1H, t, J 7.5 Hz), 6.98 (1H, t, J 7.5 Hz), 7.03–7.10 (2H, m), 7.10–7.19 (3H, m), 7.23 (1H, d, J 7.7 Hz), 7.35 (2H, d, J 8.1 Hz), 7.45 (1H, d, J 8.0 Hz), 7.53 (2H, s), 11.34 (1H, s)

FAB-MS: m/z 459.1 [MH+].

Example 9

5-[1-(4-Aminobutyl)-3-indolyl]-4-cyano-1-(1-propyl-3-indolyl)-2,3-dihydroimidazol-2-one trifluoroacetic acid salt a) (1-Carbamoyl-2-{1-[4-(1,3-dioxo-1,3-dihydroisoindol-2-yl)-butyl]-3-indolyl}-2-oxoethyl)-carbamic acid benzyl ester A mixture of 6.0 g (17 mmol) of the product obtained in Example 1b), 6.0 g (21 mmol) of N-(4-bromobutyl)-phthalimide and 9.4 g (68 mmol) of $K_2CO_3$ in 50 ml of DMF was stirred at 60° C. overnight. The mixture was partitioned between 100 ml of EtOAc and 100 ml of water. The water phase was extracted with an additional 50 ml of EtOAc, and the combined organic phases were washed with water and brine. The organic phase was evaporated, giving a solid which was washed twice with 50 ml of diethyl ether, giving the sub-title compound as a solid, 5.8 g (62%).

$^1$H-NMR (400 MHz in DMSO-$d_6$): δ 1.55–1.64 (2H, m), 1.75–1.85 (2H, m), 3.55–3.65 (2H, m), 4.20–4.35 (2H, m), 5.05 (2H, s), 5.47 (1H, d, J 7.2 Hz), 7.17–7.35 (8H, m), 7.46 (1H, d, J 7.0 Hz), 7.58–7.67 (2H, m), 7.75–7.85 (4H, m), 8.15 (1H, d, J 6.6 Hz), 8.59 (1H, s)

b) 2-amino-3-{1-[4-(1,3-dioxo-1,3-dihydroisoindol-2-yl)-butyl]-3-indolyl}-3-oxo-propionamide acetic acid salt To a solution of 5.7 g (10.3 mmol) of the product obtained in step a) in 60 ml of EtOAc and 100 ml of glacial acetic acid was added 3 g of 5% Pd(C). Hydrogenation for 4 hours followed by removal of the catalyst by filtration through celite. The filtrate was evaporated, and the residue triturated with diethyl ether and filtered to give 4.3 g (86%) of the sub-title product as a yellow solid.

$^1$H-NMR (400 MHz, DMSO-$d_6$): δ 1.60(2H, p, J 7.1 Hz), 1.80 (2H, p, J 7.4 Hz), 3.59 (2H, t, J 7.0 Hz), 4.20–4.35 (2H, m), 4.67 (1H, s), 7.15–7.30 (4H, m), 7.50–7.65 (2H, m), 7.75–7.85 (5H, m), 8.17 (1H, m), 8.51 (1H, s)

c) 1-Propylindole-3-carbonyl azide

A solution of 0.16 g (1.00 mmol) of indole-3-carboxylic acid methyl ester, 0.5 g (4 mmol) of $K_2CO_3$ and 0.5 g (5 mmol) of 1-bromopropane in 10 ml of DMF was stirred at 50° C. overnight. The mixture was partitioned between EtOAc and water. The aqueous phase was extracted with additional EtOAc. The combined organic phases were washed with water, brine and finally dried over $Na_2SO_4$ to give crude 1-propylindole-3-carboxylic acid methyl ester.

The methyl ester was dissolved in 10 ml of methanol and 10 ml of 1M NaOH and heated to reflux overnight. After most of the methanol was removed in vacuum the residual water phase was diluted to 25 ml, acidified and extracted with 3×25 ml of EtOAc. The combined organic phases were washed with brine and evaporated to give the crude 1-propylindole-3-carboxylic acid.

The crude acid was dissolved in 15 ml of $CH_2Cl_2$, 140 μl (1 mmol) of triethylamine and 0.25 g (1 mmol) of diphenyl phosphoryl azide was added. The flask was sealed and stirred overnight. The solvent was evaporated and the residue was purified by chromatography on silica ($CH_2Cl_2$:MeOH 99: 1), to give 171 mg (75%) of a reddish oil, which crystallised on standing.

$^1$H-NMR (500 MHz, CDCl$_3$): δ 0.99 (3H, t, J 7.2 Hz), 1.95 (2H, sext, J 7.4 Hz), 4.15 (2H, t, J 7.2 Hz), 7.30–7.36 (2H, m), 7.38–7.43 (1H, m), 7.86 (1H, s), 8.25–8.30 (1H, m)

FT-IR (cm$^{-1}$) 2137.1 (N=N=N-stretch)

d) 3-{1-[4-(1,3-Dioxo-1,3-dihydroisoindol-2-yl)-butyl]-3-indolyl}-3-oxo-2-[3-(1-propyl-3-indolyl)-ureido]-propionamide A solution of 57 mg (0.25 mmol) of the product of step c) in 5 ml of benzene was heated to 95° C. for 5 hours. After cooling to room temperature the benzene solution was rapidly added to a freshly prepared suspension of 120 mg (0.24 mmol) of the product of step b) and 31 mg (0.24 mmol) of ethyldiisopropylamine in 10 ml of THF. The resulting solution was stirred for 2 hours. The solvents were evaporated and the residue suspended in 20 ml of water and stirred for 10 minutes. The product was filtered and dried, giving 130 mg (84%) of the sub-title compound as a yellowish solid.

FAB-MS m/z 619.3 [MH+]

e) 4-Carbamoyl-5-{1-[4-(1,3-dioxo-1,3-dihydroisoindol-2-yl)-butyl]-3-indolyl}-1-(1-propyl-3-indolyl)-1,3-dihydroimidazol-2-one A mixture of 0.06 g (0.1 mmol) of the compound of step d), 2 ml of methanol, and a catalytic amount of scandium trifluoromethanesulfonate was heated to 105° C. for 4 hours. The reaction mixture was allowed to cool, the solvent was evaporated, and the residual purified by chromatography on silica ($CH_2Cl_2$:MeOH 97:3) to give 54 mg (93%) of the sub-title amide.

FAB-MS m/z: 601.2 [MH+]

f) 4-Cyano-5-{1-[4-(1,3-dioxo-1,3-dihydroisoindol-2-yl)-butyl]-3-indolyl}-1-[1-(ethoxycarbonyl)-3-indolyl]-1,3-dihydroimidazol-2-one A portion of 53 mg (0.088 mmol) of the product of step e) was added to 7 ml TMS-polyphosphate in $CH_2Cl_2$ and heated with stirring to 50° C. for 4 hours. After cooling to room temperature the solution was diluted to 20 ml with $CH_2Cl_2$ and washed with 10 ml of water. The aqueous phase was extracted with an additional 10 ml of $CH_2Cl_2$, the combined organic phases were washed with water and brine. The solvent was removed in vacuum and the residue purified by chromatography on silica ($CH_2Cl_2$:MeOH 97:3), to give 34 mg (66%) of the sub-title compound as an orange solid.

$^1$H-NMR (500 MHz, CDCl$_3$): δ 0.76 (3H, t, J 7.3 Hz), 1.35 (2H, p, J 7.5 Hz), 1.60–1.66 (2H, m), 1.75 (2H, sext, J 7.4 Hz), 3.54 (2H, t, J 7.1 Hz), 4.02 (2H, q, J 8.0 Hz), 6.98–7.06 (3H, m), 7.12–7.19 (3H, m), 7.25–7.32 (3H, m), 7.43 (1H, d, J 8.2 Hz), 7.71–7.75 (2H, m), 7.18–7.87 (2H, m), 8.79 (1H, bs)

FAB-MS m/z: 583.2 [MH+]

A portion of 34 mg (0.058 mmol) of the product of step f) was dissolved in 10 ml of THF, and 3 ml of aqueous methylamine (40%) and stirred for 3 hours. The solvent was removed in vacuum and the residue purified by preparative HPLC (C 18-reversed phase, acetonitrile-water trifluoroacetic acid). The title compound was obtained after lyophilization, giving 25 mg (76%) as a white solid.

$^1$H-NMR (400 MHz, DMSO-$d_6$): δ 0.63 (3H, t, J 7.5 Hz), 1.28 (2H, p, J 7.4 Hz), 1.54–1.67 (4H, m), 2.62–2.71 (2H, m), 4.06 (4H, t, J 6.7 Hz), 6.86–6.96 (2H, m), 7.04–7.15 (3H, m), 7.34–7.46 (4H, m), 7.54 (1H, s), 7.57 (3H, bs), 11.37 (1H, s)

FAB-MS m/z: 453.1 [MH+]

Example 10

5-[1-(4-Aminobutyl)-3-indolyl]-4-cyano-1-(4-methoxyphenyl)-2,3-dihydroimidazol-2-one trifluoroacetic acid salt

The title product was prepared according to the procedure of Example 9, starting from the product of Example 9b), and 1-isocyanato-4-methoxybenzene.

APCI-MS m/z: 402.2 [MH+].

Example 11

5-[1-(4-Aminobutyl)-3-indolyl]-4-cyano-1-(4-phenoxyphenyl)-2,3-dihydroimidazol-2-one trifluoroacetic acid salt The title product was prepared according to the procedure of Example 9, starting from the product of Example 9b), and 1-isocyanato-4-phenoxybenzene.

APCI-MS m/z: 464.0 [MH+].

Example 12

5-[1-(4-Aminobutyl)-3-indoyl]-1-(4-tert-butylphenyl)-4-cyano-2,3-dihydroimidazol-2-one trifluoroacetic acid salt The title product was prepared according to the procedure of Example 9, starting from the product of Example 9b), and 1-isocyanato-4-tert-butylbenzene.

APCI-MS m/z: 428.0 [MH+].

Example 13

5-[1-(4-Aminobutyl)-3-indoyl]-4-cyano-1-(3-nitrophenyl)-2,3-dihydroimidazol-2-one trifluoroacetic acid salt The title product was prepared according to the procedure of Example 9, starting from the product of Example 9b), and 1-isocyanato-3-nitrobenzene.

$^1$H-NMR (300 MHz, CDCl$_3$): δ 1.47 (2H, p, J 7.6 Hz), 1.83 (2H, p, J 7.6 Hz), 2.75–2.81 (2H, m), 4.20 (2H, t, J 6.5 Hz), 6.88 (1H, t, J 8.0 Hz), 7.04–7.14 (2H, m), 7.35–7.50 (2H, m), 7.60–7.66 (1H, m), 7.99–8.04 (1H, m) 8.13 (1H, t, J 2.1 Hz)

FAB-MS m/z: 417.1 [MH+].

Example 14

5-[1-(4-Aminobutyl)-3-indoyl]-4-cyano-1-[(4-ethoxycarbonyl)phenyl]-2,3-dihydroimidazol-2-one acetic acid salt The title product was prepared according to the procedure of Example 9, starting from the product of Example 9b), and 4-isocyanato-1-benzoic acid ethyl ester.

FAB-MS m/z: 444.2 [MH+].

Example 15

5-[1-(4-Aminobutyl)-3-indoyl]-4-cyano-1-(1-naphthyl)-2,3-dihydroimidazol-2-one acetic acid salt The title product was prepared according to the procedure of Example 9, starting from the product of Example 9b), and 1-naphthylisocyanate.

FAB-MS m/z: 408.3 [MH+].

Example 16

4-Cyano-5-(3-indolyl)-1-(1-naphthyl)-2,3-dihydroimidazol-2-one

The title product was prepared according to the procedure of Example 9, starting from the product of Example 1c), and 1-naphthylisocyanate.

FAB-MS m/z: 351.0 [MH+]

Example 17

4-Cyano-5-[1-(3-(N-isopropylamino)propyl)-3-indolyl]-1-(1-methyl-3-indolyl)-2,3-dihydroimidazol-2-one trifluoroacetic acid salt a) 2-(2,4-Dimethoxybenzylamino)-3-(3-indolyl)-3-oxo-propionamide A solution of 2.0 g (5.69 mmol) of [1-carbamoyl-2-(3-indolyl)-2-oxoethyl]-carbamic acid benzyl ester in 160 ml ethyl acetate:acetic acid:ethanol (1:2:1) was hydrogenolyzed at atmospheric pressure over 0.45 g of 10% Pd(C) for 3 h. The mixture was filtered and concentrated. 2.41 g (11.4 mmol) of NaBH(OAc)$_4$ was added in portions to a solution of the residue and 0.95 g (5.69 mmol) of 2,4-dimethoxybenzaldehyde in 30 ml of DMF:HOAc (1:1). After 18 h at room temperature the reaction mixture was concentrated and purified by chromatography on SiO$_2$ (PhMe—CH$_2$Cl$_2$—MeOH—NEt$_3$, 30:60:20:2). The solid product was washed with ether to give the title compound (1.78 g, 85%).

$^{13}$C-NMR (400 MHz, DMSO-d6): δ 45.4, 55.1, 55.2, 68.2, 98.2, 104.2, 112.2, 115.0, 120.2, 121.3, 121.9, 122.9, 125.6, 129.4, 135.6, 136.4, 157.9, 159.5, 171.2, 190.4.

APCI-MS: m/z 368 [MH+]

b) 4-Cyano-3-(2,4-dimethoxybenzyl)-5-(3-indolyl)-1-(1-methyl-3-indolyl)-2,3-dihydroimidazol-2-one A solution of 0.30 g (1.5 mmol) of 1-methylindole-3-carbonyl azide in 15 ml of benzene was heated to reflux for 5 h, cooled and added to a solution of 0.55 g (1.5 mmol) of the product from step a) in 30 ml of THF. After 1h at room temperature and 4 h at 50° C. the mixture was concentrated. The residue was dissolved in 40 ml of EtOH:HOAc (4:1) and heated to reflux for 45 minutes and concentrated to give a solid material. The major part of the solid material (93%), 15 ml of acetonitrile and 30 ml of TMS-polyphosphate solution in CH$_2$Cl$_2$ was heated to reflux for 1.5 h. The brown solution was cooled and carefully added to a stirred mixture 100 ml of CH$_2$Cl$_2$, 200 ml of NaHCO$_3$(aq) and 20 ml of MeOH. The organic layer was concentrated and the residue purified by silica gel chromatography (PhMe:EtOAc, 1:1), to give the sub-title compound (0.44 g, 63%).

$^{13}$C-NMR (400 MHz, DMSO-d6): δ 32.6, 41.4, 55.2, 55.4, 93.7, 98.5, 100.4, 104.7, 108.8, 110.3, 112.0, 112.6, 116.1, 117.3, 119.2, 119.9, 119.8, 121.8, 122.0, 124.4, 124.8, 126.9, 128.4, 129.5, 133.2, 135.0, 135.5, 151.7, 157.9, 160.5.

APCI-MS: m/z 504 [MH+]

c) 3-{3-[5-Cyano-1-(2,4-dimethoxybenzyl)-3-(3-indolyl)-2-oxo-2,3-dihydro-1H-imidazol-4-yl]-1-indolyl}-propyl methanesulfonate To a solution 0.15 g (0.298 mmol) of the product from step b) in 2 ml of DMF was 0.40 g (1.72 mmol) of 1,3-propandiol bismethansulfonate and 0.50 g (3.62 mmol) of K$_2$CO$_3$. The mixture was stirred at 70° C. overnight and partitioned between EtOAc and water. The organic phase was washed with water and brine and finally evaporated. The residue was purified by chromatography on silica furnishing 0.11 g (59%) of the sub-title compound.

$^1$H-NMR (400 MHz, CDCl$_3$): δ 1.95 (2H, p, J 6.2 Hz), 2.79 (3H, s), 3.69 (2H, t, J 5.3 Hz), 3.74 (3H, s), 3.84 (3H, s), 3.94 (3H, s), 4.13 (2H, t, J 5.9 Hz), 5.04 (2H, s), 6.50 (1H, s), 6.52 (1H, s), 6.93 (1H, t, J 7.5 Hz), 7.00 (1H, s), 7.08–7.18 (3H, m), 7.19–7.29 (4H, m), 7.44 (1H, d, J 8.0 Hz), 7.52 (1H, d, J 8.0 Hz)

APCI-MS: m/z 640.0 [MH+].

d) 4-Cyano-3-(2,4-dimethoxybenzyl)-5-[1-(3-isopropylaminopropyl)-3-indolyl]-1-(1-methyl-3-indolyl)-2,3dihydroimidazol-2-one A mixture of 47 mg (0.078 mmol) of the product of step c) and 10 ml of isopropylamine was stirred overnight. Excess amine was removed in vacuum, giving 46 mg of the sub-title product as a yellow oil.

APCI-MS m/z: 603.2 [MH+].

A mixture of 46 mg (0.078 mmol) of the product of step d), 20 ml of acetonitrile and 0.5 ml of triflic acid was stirred at 70° C. for 2 hours. The mixture was partitioned between 50 ml of EtOAc and 50 ml of 1M NaOH. The aqueous phase was extracted with 3×20 ml of EtOAc, and the combined organic phases were washed with brine. The solvent was removed in vacuum and the residue purified by preparative HPLC (C18-reversed phase, acetonitrile-water trifluoroacetic acid). The title compound was obtained after lyophilization, giving 25 mg (57%) as a colourless oil.

$^1$H-NMR (400 MHz, CD$_3$OD): δ 1.08 (6H, d, J 6.4 Hz), 1.82–1.93 (2H, m), 2.86 (1H, hept, J 6.9 Hz), 3.67 (2H, t, J 6.3 Hz), 3.73 (3H, s), 4.15 (2H, t, J 6.8 Hz), 6.95 (1H, d, J 8.4 Hz), 7.00 (1H, t, J 7.4 Hz), 7.10–7.20 (3H, m), 7.22 (1H, s), 7.30 (1H, s), 7.32–7.44 (3H, m)

APCI-MS m/z: 453.0 [MH+].

Example 18

5-[-1(S)-(3(S)-Aminocyclopentyl)-3-indolyl]-4-cyano-1-(1-methyl-3-indolyl)-2,3-dihydroimidazol-2-one acetic acid salt.

a) 4-Cyano-3-(2,4-dimethoxybenzyl)-5-{1(S)-[3(S)-(1,3-dioxo-1,3-dihydroisoindol-2-yl)-cyclopentyl]-3-indolyl}-1-(1-methyl-3-indolyl)-2,3-dihydroimidazol-2-one Two portions of totally 0.72 g (2.33 mmol) of 1(R)-O-Methanesulfonyl-3(S)-phthalimido-cyclopentane and two portions of totally 1.33 g (4.05 mmol) of cesium carbonate were added within 1.5 hours, to a stirred solution of 0.26 g (0.51 mmol) 4-cyano-3-(2,4-dimethoxybenzyl)-5-(3-indolyl)-1-(1-methyl-3-indolyl)-2,3-dihydroimidazol-2-one in 3 ml of dry DMF at 70° C. After an additional 2 hours, the reaction mixture was cooled to room temperature and partitioned between ethyl acetate and saturated brine. The aqeous phase was back-extracted with ethyl acetate and the combined organic extracts washed three times with saturated brine, dried over Na$_2$SO$_4$ and concentrated. The residue was purified by chromatography on SiO$_2$ (EtOAc-heptane, 3:2). The fractions containing the desired product were combined and crystallized (chloroform:ether) to give the sub-title compound (0.20 g, 54%).

$^1$H-NMR (400 MHz, CDCl$_3$): δ 1.58 (1H, m), 1.79 (2H, m), 2.01 (1H, m), 2.31 (1H, m), 2.50 (1H, m), 3.77 (3H, s), 3.83 (3H, s), 3.94 (3H, s), 4.56 (1H, m), 5.07 (2H, s), 5.14 (1H, m), 6.52 (1H, s), 6.93 (1H, s), 7.00 (1H, m), 7.13–7.28 (7H, m), 7.38 (1H, d, J 8.2), 7.43 (1H, d, J 8.4 Hz), 7.60 (1H, d, J 7.8 Hz), 7.72–7.76 (2H, m), 7.83–7.87 (2H, m)

b) 4-Cyano-5-{1(S)-[3(S)-(1,3-dioxo-1,3-dihydroisoindol-2-yl)-cyclopentyl]-3-indolyl}-1-(1-methyl-3-indolyl)-2,3-dihydroimidazol-2-one A refluxing solution of 0.14 g (0.20 mmol) of the product from step a) in 15 ml of dry acetonitrile was treated with 1.3 ml of trimethylsilyl bromide in three portions over a period of 24 hours. The reaction mixture was refluxed for an additional 6 hours. After cooling to room temperature 5 ml of methanol was added and the mixture was concentrated. The residue was purified by chromatography on SiO$_2$ (toluene:ethyl acetate, 1:2) to afford the sub-tidtle compound (55 mg, 49%).

$^1$H-NMR (400 MHz, acetone-d6): δ 1.72 (m, 1H), 1.84 (1H, m), 1.94 (1H, m), 2.10 (1H, m), 2.36 (1H, m), 2.88 (1H, m), 3.84 (3H, s), 4.67 (1H, m), 5.26 (1H, m), 6.96 (1H, dt, J 1.0, 8.0 Hz), 7.12 (2H, m), 7.21 (1H, m), 7.25 (1H, d, J 8.0 Hz), 7.30 (1H, s), 7.40 (1H, d, J 8.4 Hz), 7.46 (1H, s), 7.50 (1H, d, J 8.2 Hz), 7.68 (1H, d, J 7.8 Hz), 7.83–7.88 (4H, m)

A solution of 0.055 g (0.10 mmol) of the product from step b) in 6 ml of THF was treated with 0.6 ml of aqueous methylamine (40%), the mixture was left at room temperature for 3 days and then concentrated. The residue purified by chromatography on SiO$_2$ (CH$_2$Cl$_2$:methanol:ammonia, 150:10:1 followed by 150:15:3) to give the free amine as a solid. The solid treated with acetic acid and freeze-dried to give the title compound (40 mg, 83%).

$^{13}$C-NMR (400 MHz, DMSO-d6): δ 30.7, 32.6, 32.9, 41.2, 50.7, 54.9, 79.2, 89.9, 100.3, 108.8, 110.2, 110.6, 113.5, 117.3, 119.6, 119.8, 120.2, 121.8, 122.0, 124.5, 125.2, 126.6, 128.4, 133.5, 135.0, 135.4, 152.3, 172.4.

Example 19

1-[1-(3-Aminopropyl)-3-indolyl]-4-cyano-5-(1-methyl-3-indolyl)-2,3-dihydroimidazol-2-one hydrochloric acid salt a) 4-Cyano-5-(1-methyl-3-indolyl)-1-[1-(2,2,2-trichloroethoxycarbonyl)-3-indolyl]-2,3-dihydroimidazol-2-one This compound was prepared in a manner analogous to Example 1, starting from 3-(azidocarbonyl)-1-(2,2,2-trichloroethoxycarbonyl)indole (Sovorov et al Khimiya Gereotsiklicheskikh Soedinenii 8, (1975), 1099–1105) and 2-amino-3-(3-indolyl)-3-oxopropionamide acetic acid salt.

$^1$H NMR (400 MHz, DMSO-d6): δ 3.73 (3H, s), 5.23 (2H, s), 6.97 (1H, bt), 7.11–7.42 (6H, m), 7.54 (1H, s), 7.90 (1H, s), 8.08 (1H, d, J 8.2 Hz), 11.56 (1H, bs, NH)

APCI-MS: m/z 530 [MH+]

b) 3-(tert-Butoxycarbonyl)-4-cyano-5-(1-methyl-3-indolyl)-1-[1-(2,2,2-trichloroethoxycarbonyl)-3-indolyl]-2,3-dihydroimidazol-2-one A solution of 0.24 g (0.45 mmol) of the product from step a), 0.13 g (0.59 mmol) of di-tert-butyl dicarbonate and 0.005 g (0.04 mmol) of 4-dimethylaminopyridine in 10 ml of dry THF was stirred at room temperature for 2 hours. 1 g of SiO$_2$ was added and the solvent removed the residue was purified by chromatography on SiO$_2$ (heptan:ethyl acetate) furnished the sub-title compound (267 mg, 94%).

$^1$H-NMR (500 MHz, DMSO-d6): δ 1.60 (9H, s), 3.72 (3H, s), 5.24 (2H, s), 6.98 (1H, bt), 7.14 (1H, bt), 7.23 (1H, bt), 7.37 (1H, bt), 7.41 (1H, d, J 8.3 Hz), 7.45 (1H, d, J 7.9 Hz), 7.50 (1H, d, J 7.7 Hz), 7.59 (1H, s), 7.96 (1H, s), 8.07 (1H, d, J 8.3 Hz).

APCI-MS: m/z 530 [(MH-tBoc)+]

c) 3-(tert-Butoxycarbonyl)-4-cyano-5-(1-methyl-3-indolyl)-1-(3-indolyl)-2,3-dihydroimidazol-2-one To a suspension of 0.26 g (0.41 mmol) of the product from step b) in 5 ml of DMF was added 0.27 g (4.1 mmol) zinc powder, 0.028 g (0.12 mmol) of cadmium chloride and 5 ml of acetic acid. The mixture was sonicated for 2 minutes and stirred at room temperature for 30 minutes. Water and ethyl acetate were added, the phases were separated and the organic phase washed with saturated NaHCO$_3$(aq), dried over Na$_2$SO$_4$ and evaporated. The residue was purified by chromatography on SiO$_2$ (toluene:ethyl acetate) fuishing the sub-title compound (150 mg, 80%).

$^1$H-NMR (400 MHz, DMSO-d6): δ 1.60 (9H, s), 3.69 (3H, s,), 6.92–7.01 (2H, m), 7.07 (1H, bt), 7.14 (1H, bt), 7.33 (1H, d, J 8.8 Hz), 7.39 (1H, d, J 8.4 Hz), 7.43 (1H, d, J 8.2 Hz), 7.48 (1H, s), 7.52 (1H, d, J 2.7 Hz), 11.31 (1H, bd, J 2.3 Hz, NH).

APCI-MS: m/z 354 [(MH-tBoc)+]

d) 3-(tert-Butoxycarbonyl)-4-cyano-5-(1-methyl-3-indolyl)-1-{1-[3-(1,3-dioxo-1,3-dihydroisoindol-2-yl)-propyl]-3-indolyl}-2,3-dihydroimidazol-2-one To a suspension of 0.12 g (0.28 mmol) of the product from step c) and 0.15 g (1.1 mmol) of $K_2CO_3$ in dry 5 ml of DMF was added 0.083 g (0.30 mmol) of N-(3-bromopropyl)-phthalimide. The mixture was stirred at room temperature overnight and then partitioned between water and ethyl acetate. The aqueous phase was extracted with ethyl acetate and the combined organic phases were washed with water, brine, dried over $Na_2SO_4$ and evaporated. Chromatography on $SiO_2$ (heptan-ethyl acetate) gave the title compound (152 mg, 86%).

$^1$H-NMR (400 MHz, DMSO-d6): δ 1.60 (9H, s), 2.21 (2H, m), 3.69 (3H, s), 3.74 (2H, bt), 3.89 (2H, bt), 7.03 (1H, bt), 7.12 (1H, bt), 7.17 (1H, bt), 7.21 (1H, d, J 7.8 Hz), 7.30 (1H, bt), 7.42 (1H, d, J 8.2 Hz), 7.43 (1H, s), 7.47 (1H, d, J 7.8 Hz), 7.82–7.90 (5H, m), 8.00 (1H, d, J 8.4 Hz)

APCI-MS: m/z 641 [MH+]

To a solution of 0.14 g (0.22 mmol) of the product from step d) in THF (5 mL) was added 5 ml of aqueous methylamine (40%). After 1.5 hours at room temperature the volatiles were removed and the residue purified by chromatography on $SiO_2$ ($CH_2Cl_2$:methanol:ammonia) gave free amine (70 mg, 77%). The amine was dissolved in $CH_2Cl_2$:methanol (2:3) and 0.1 M HCl(aq) was added. The mixture was concentrated and lyophilized to give the title compound (76mg, 100%).

$^1$H-NMR (400 MHz, DMSO-d6): δ 1.86 (2H, m), 2.69 (2H, bt), 3.68 (3H, s), 3.87 (2H, bt), 6.94 (1H, bt), 6.99 (1H, bt), 7.07 (1H, bt), 7.12–7.19 (2H, m), 7.33–7.42 (4H, m), 7.53 (1H, s), 11.34 (1H, bs, NH).

FAB-MS: m/z 411 [MH+]

The following compounds were made in analogous manner to the Examples above:

Example 20

5-[1-(4-Aminobutyl)-3-indolyl]-4-cyano-1-(3-indolyl)-2,3-dihydroimidazol-2-one trifluoroacetic acid salt $^1$H-NMR (400 MHz, DMSO-d6): δ 1.27 (2H, p, J 7.5 Hz), 1.60 (2H, p, J 7.5 Hz), 2.67–2.74 (2H, m), 4.10 (2H, t, J 7.0 Hz), 6.92 (1H, t, J 7.5 Hz), 7.01 (1H, t, J 7.2 Hz), 7.08 (1H, t, J 7.7 Hz), 7.13–7.18 (2H, m), 7.35 (1H, d, J 7.1 Hz), 7.36 (1H, s), 7.44 (1H, d, J 8.0 Hz), 7.48 (1H, d, 8.4 Hz), 7.51 (1H, d, J 2.7 Hz), 7.59 (3H, bs), 11.29 (1H, s), 11.39 (1H, s)

FAB-MS: m/z 411.1 [MH+]

Example 21

5-[1-(2-Aminoethyl)-3-indolyl]-4-cyano-1-(3-indolyl)-2,3-dihydroimidazol-2-one trifluoroacetic acid salt $^1$H-NMR (400 MHz, DMSO-d6): δ 3.04 (2H, t, J 6.7 Hz), 4.24 (2H, t, J 6.8 Hz), 6.94 (1H, t J 7.2 Hz), 7.03–7.11 (2H, m), 7.18 (1H, d, J 7.8 Hz), 7.20 (1H, t, J 7.2 Hz), 7.37 (1H, d, J 8.2 Hz), 7.39 (1H, s), 7.47 (1H, d, J 8.0 Hz), 7.48–7.52 (2H, m), 11.30 (1H, s)

FAB-MS: m/z 383.0 [MH+]

Example 22

5-{1-[4-(Aminomethyl)benzyl]-3-indolyl}-4-cyano-1-(1-methyl-3-indolyl)-2,3-dihydroimidazol-2-one trifluoroacetic acid salt $^1$H-NMR (400 MHz, DMSO-d6): δ 3,77 (3H, s), 3,94 (2H, m), 5.31 (2H, s), 6.85 (2H, d), 6.93 (1H, t), 7.01 (1H, t), 7.06 (1H, t), 7.13 (1H, d), 7.17 (1H, t), 7.23 (2H, d), 7.45 (1H, d), 7.49 (1H, d), 7.53 (1H, s), 7.61 (1H, s), 8.08 (3H, s), 11.41 (1H, s)

FAB-MS: m/z 473.3 [MH+]

Example 23

5-{1-[2-(Aminomethyl)benzyl]-3-indolyl}-4-cyano-1-(1-methyl-3-indolyl)-2,3-dihydroimidazol-2-one trifluoroacetic acid salt $^1$H-NMR (400 MHz, DMSO-d6): δ 3,71 (3H, s), 4.01 (2H, bs), 5.48 (2H, s), 5.76 (1H, d), 6.90 (1H, t), 6.95 (1H, t), 7.17–7.06 (4H, m), 7.22 (1H, s), 7.29 (1H, t), 7.35 (1H, d), 7.39 (1H, d), 7.41 (1H, d), 7.57 (1H, s), 7.59 (1H, d), 8.19 (3H, bs), 11.43 (1H, s)

FAB-MS: m/z 473.3 [MH+]

Example 24

5-[1-(3-Aminopropyl)-3-indolyl]-4-cyano-1-(1-methyl-3-indolyl)-2,3-dihydroimidazol-2-one trifluoroacetic acid salt $^1$H-NMR (400 MHz, DMSO-d6): δ 1.86 (2H, p, J 6.8 Hz), 2.54 (2H, t, J 7.6 Hz), 3.75 (3H, s), 1.86 (2H, p, J 6.8 Hz), 4.17 (2H, t, J 6.4 Hz), 6.92 (1H, t, J 7.2 Hz), 7.01 (1H, t, J 7.6 Hz), 7.17–7.07 (3H, m), 7.41 (1H, d, J 9.2 Hz), 7.43 (1H, d, J 8.0 Hz), 7.45 (1H, s), 7.48 (1H, d, J 8.0 Hz), 7.57 (1H, s), 7.74 (3H, bs)

FAB-MS: m/z 411.0 [MH+]

Example 25

4-Cyano-5-[1-(4-methoxybenzyl)-3-indolyl]-1-(1-methyl-3-indolyl)-2,3-dihydroimidazol-2-one $^1$H-NMR (400 MHz, DMSO-d6): δ 3.69 (3H, s), 3.75 (3H, s), 5.19 (2H, s), 6.67 (2H, d, J 8.8 Hz), 6.73 (2H,d, J 8.8 Hz), 6.92 (1H, t, J 8.0 Hz), 7.20–7.00 (4H, m), 7.39 (1H, d, J 8.0 Hz), 7.39 (1H, s), 7.46 (1H, d, J 8.0 Hz), 7.52 (1H, d, J 8.0 Hz), 7.56 (1H, s), 11.38 (1H, s)

FAB-MS: m/z 474.0 [MH+]

Example 26

5-{1-[3-(Aminomethyl)benzyl]-3-indolyl}-4-cyano-1-(1-methyl-3-indolyl)-2,3-dihydroimidazol-2-one trifluoroacetic acid salt $^1$H-NMR (400 MHz, DMSO-d6): δ 3.77 (3H, s), 3.95 (2H, m), 5.33 (2H, s), 6.58 (1H, d, J 8.0 Hz), 6.94 (1H, t, J 7.5 Hz), 7.04 (1H, t, J 7.5 Hz), 7.11 (1H, t, J 7.6 Hz), 7.13–7.22 (3H, m), 7.29 (1H, s), 7.31 (1H, d, J 7.6 Hz), 7.37 (1H, d, J 8.2 Hz), 7.46 (1H, d, J 8.2 Hz), 7.52 (1H, d, J 7.8 Hz), 7.54 (1H, s), 7.61 (1H, s), 8.11 (3H, bs), 11.43 (1H, s)

Example 27

5-{1-[5-(Aminomethyl)-2-thiophenylmethyl]-3-indolyl}-4-cyano-1-(1-methyl-3-indolyl)-2,3-dihydroimidazol-2-one hydrochloride a) (3-Indolyl)-3-oxo-2-(2,4,6-trimethoxybenzylamino) propionamide A solution of ([1-carbamoyl-2-(3-indolyl)-2-oxoethyl]-carbamic acid benzyl ester (2.0 g, 5.69 mmol) in ethyl acetate-acetic acid-ethanol (1:2:1, 160 ml) was hydrogenolyzed at atmospheric pressure over 10% Pd(C) (0.45 g) for 15 hours. The mixture was filtered and concentrated.

Sodium triacetoxyborhydride (2.41 g, 11.38 mmol) was added in portions to a solution of the residue and 2,4,6-trimethoxybenzaldehyde (1.12 g, 5.69 mmol) in DMF-acetic acid (1:1, 50 ml). After 18 hours at room temperature the reaction mixture was concentrated and the residue was treated with $Na_2CO_3$(aq) (0.4 M, 120 ml). The solid product formed was washed with water (3×30 ml) and ether (3×20 ml) and dried under vacuum at 50° C. for 6 hours, to give the title compound (1.70 g, 75%).

APCI-MSMS m/z: 400 [MH+].

$^{13}$C-NMR (400, MHz, DMSO-d6): δ 190.7, 171.3, 160.1, 158.8(2C), 136.3, 135.4, 125.6, 122.8, 121.7, 121.3, 115.0, 112.1, 108.0, 90.6, 68.2, 55.6(2C), 55.1.

APCI-MS m/z: 398 [MH+].

b) 4-Cyano-3-(2,4,6-trimethoxybenzyl)-5-(3-indolyl)-1-(1-methyl-3-indolyl)-2,3-dihydroimidazol-2-one 1-Methylindole-3-carbonyl azide (1.59 g, 7.96 mmol) in toluene (100 ml) was reflux for 50 minutes, cooled and concentrated. The residue and the product from step a) (1.58 g, 3.98 mmol) in THF (150 ml) was heated at the reflux temperature for 18 hours, cooled and concentrated. The solid residue was washed with ether (3×30 ml), THF (5 ml) and ether (30 ml). Yield 1.45 g (66%) of the corresponding carboxamide of tide compound.

APCI-MS m/z: m/z: 552 [MH+].

Triphenylphosphine (1.31 g, 5 mmol) was added in portions during 2 minutes carboxamide (0.55 g, 1.0 mmol), triethylamine (1.39 ml, 10 mmol) and carbontetrachloride (0.58 ml, 6 mmol) in acetonitrile (20 ml), at room temperature. After 17 hours, water (0.3 ml) was added drop wise and the reaction mixture was concentrated. The residue was purified by silica gel chromatography (dichloromethane:acetone, 1:1), to give the tide compound (0.38 g, 71%).

$^1$H-NMR (400, MHz, DMSO-d6): δ 3.73 (3H, s), 3.81 (3H, s), 3.82 (6H, s), (2H, s), 6.30 (2H, s), 6.98 (2H, bq), 7.08 (1H, bt, J 7.4 Hz), 7.13 (2H, m), 7.23 (1H, d, J 2.7 Hz), 7.33 (1H, d, J 8.2 Hz), 7.36 (1H, d, J 8.0 Hz), 7.42 (1H, d, J 8.6 Hz), 7.55 (1H, s), 11.44 (1H, s).

APCI-MS m/z: 534 [MH+].

c) (5-Bromomethyl-2-thiophenylmethyl)isoindole-1,3-dione

Azoisobutyronitrile (0.192 g, 0.53 mmol) was added to 2,5-fimethylthiophene (2.0 g, 17.8 mmol) and N-bromosuccinimide (6,99 g, 39.3 mmol) in carbontetrachloride (25 ml). After heating to reflux for 20 min., the reaction mixture was cooled, filtered and concentrated. The residue was dissolved in acetonitrile (50 ml) and potassium phthalimide (2.31 g, 12.4 mmol) and tetrabutylammonium bromide (0.574 g, 1.78 mmol) was added. After 64 hours at room temperature ethyl acetate (50 ml) was added and the mixture filtered and concentrated. The residue was chromatographed on silica gel. After removal of solvent the residue was tirturated with petroleum ether 40–60° C. (75 ml) to afford a the sub-title product as a crystalline solid, 1.22 g (29%).

$^1$H-NMR (400 MHz, CDCl$_3$): δ 4.65 (2H, s), 4.95 (2H, s), 6.94 (1H, d, J 3.7 Hz), 6.97 (1H, d, J 3.7 Hz), 7.72 (2H, m), 7.86 (2H, m).

The product from step b) (55 mg, 0.10 mmol), (5-Bromomethyl-thiophen-2-ylmethyl)-isoindole-1,3-dione (40 mg, 0.12 mmol), $Cs_2CO_3$ (98 mg, 0.30 mmol) and acetonitrile (1 ml) was heated for 50° C. for 1 hours. The reaction mixture was filtered through a plug of silica gel and concentrated. To the residue and sodium iodide (75 mg, 0.5 mmol) was added a solution of borontriflouride etherate (0.126 ml, 1.0 mmol) in acetonitrile (0.5 ml), and the mixture was heated at 50° C. for 50 min. The mixture was cooled, treated with 40% MeNH2(aq) (0.2 ml) and concentrated. The residue and 40% MeNH2(aq) (1.5 ml) in THF (2 ml) was heated at 50° C. for 100 min. The reaction mixture was concentrated and residue was chromatographed on silica gel (dichloromethane:methanol:ammonium hydroxide, 120:10:1). Appropriate fractions were combined and concentrated and the residue was coevaporated several times with methanol. The obtained free amine in methanol (2 ml) was acidified with HCl (aq) (0.4 M, 0.3 ml), and the solution was concentrated and cooncentrated with methanol two times to give 14 mg (27%) of the title compound.

$^1$H-NMR (400 MHz, CD$_3$OD): δ 3.73 (3H, s), 4.16 (2H, s), 5.36 (2H, s), 6.50 (1H, d, J 3.6 Hz), 6.93 (1H, bd, J 3.6 Hz), 6.97 (1H, d, J 8.2 Hz), 7.05 (1H, bt, J 7.5 Hz), 7.16 (3H, m), 7.21 (1H, s), 7.32 (1H, s), 7.35 (1H, d, J 8.4 Hz), 7.39 (1H, d, J 8.2 Hz), 7.51 (1H, d, J 8.0 Hz).

LC/APCI-MS m/z: 479 [MH+].

Example 28

4-Cyano-1-(3-indolyl)-5-(1-methyl-3-indolyl)-2,3-dihydroimidazol-2-one $^1$H-NMR (400 MHz, DMSO-d6): δ 3.68 (3H, s), 6.93 (1H, bt), 6.96 (1H, bt), 7.06 (1H, bt), 7.12 (1H, bt), 7.20 (1H, d, J 7.8 Hz), 7.33 (1H, d, J 8.2 Hz), 7.37–7.40 (3H, m), 7.49 (1H, d, J 2.7 Hz), 11.25 (1H, bd, J 2.3 Hz, NH), 11.35 (1H, bs, NH)

FAB-MS: m/z 354 [MH+]

Example 29

4-Cyano-1,5-bis-(1-methyl-3-indolyl)-2,3-dihydroimidazol-2-one $^1$H-NMR (400 MHz, DMSO-d6): δ 3.67 (3H, s), 3.73 (3H, s), 6.95 (1H, bt), 7.00 (1H, bt), 7.10–7.20 (3H, m), 7.37–7.44 (4H, m), 7.55 (1H, s), 11.36 (1H, bs, NH)

FAB-MS: m/z 368 [MH+]

Example 30

4-Cyano-5-[1-(N,N-dimethylaminopropyl)-3-indolyl]-1-(1-methyl-3-indolyl)-2,3-dihydroimidazol-2-one trifluoroacetic acid salt $^1$H-NMR (400 MHz, DMSO-d6): δ 1.87–1.96 (2H, m), 2.64 (3H, s), 2.65 (3H, s), 2.80–2.87 (2H, m), 3.73 (3H, s), 4.12 (2H, t, J 7.0 Hz), 6.91 (1H, t, J 7.6 Hz), 7.00 (1H, t, J 7.6 Hz), 7.07–7.18 (3H, m), 7.38–7.49 (4H, m), 7.56 (1H, s), 9.23 (1H, bs), 11.39 (1H, s)

APCI-MS: m/z 439.0 [MH+]

Example 31

5-{1-[6-(Aminomethyl)-2-pyridylmethyl]-3-indolyl}-1-(1-methyl-3-indolyl)-2,3-dihydroimidazol-2-one bis trifluoroacetic acid salt $^1$H-NMR (400 MHz, DMSO-d6): δ 3.72 (3H, s), 4.13 (2H, q, J 5.7 Hz), 5.39 (2H, s), 6.13 (1H, d, J 7.9 Hz), 6.87 (1H, t, J 8.1 Hz), 7.00–7.14 (4H, m), 7.27–7.33 (2H, m), 7.40 (1H, d, J 9.1 Hz), 7.48–7.55 (3H, m), 7.58 (1H, s), 8.22 (3H, bs), 11.41 (1H, s)

FAB-MS: m/z 474.2 [MH+]

Example 32

5-[1-(4-Aminobutyl)-3-indolyl]-4-cyano-1-(1-methyl-3-indolyl)-2,3-dihydroimidazol-2-one trifluoroacetic acid salt $^1$H-NMR (400 MHz, DMSO-d6): δ 1.25 (2H, p, J 7.4 Hz), 1.59 (2H, p, J 7.7 Hz), 2.63–2.73 (2H, m), 3.77 (3H, s), 4.10

(2H, t, J 6.8 Hz), 6.94 (1H, t, J 7.4 Hz), 7.05 (1H, t, J 7.3 Hz), 7.11–7.19 (3H, m), 7.36 (1H, s), 7.44 (1H, d, J 8.4 Hz), 7.48 (1H, d, J 8.2 Hz), 7.49 (1H, d, J 8.2 Hz), 7.58 (1H, s), 7.63 (2H, bs), 11.41 (1H, s).

FAB-MS m/z: 425.2 [MH+].

Example 33

4-Cyano-5-[1-(3-{methylamino}propyl)-3-indolyl]-1-(1-methyl-3-indolyl)-2,3-dihydroimidazol-2-one trifluoroacetic acid salt $^1$H-NMR (500 MHz, DMSO-d6): δ 1.90 (2H, p, J 7.6 Hz), 2.47 (3H, t, J 5.4 Hz), 2.61–2.68 (2H, m), 3.77 (3H, s), 4.19 (2H, t, J 6.8 Hz), 6.94 (1H, t, J 7.4 Hz), 7.04 (1H, t, J 7.4 Hz), 7.11–7.20 (3H, m), 7.44 (1H, d, J 8.1 Hz), 7.47 (1H, d, J 8.7 Hz), 7.48 (1H, s), 7.50 (1H, d, J 8.3 Hz), 7.60 (1H, s), 8.27 (2H, bs), 11.43 (1H, s).

FAB-MS m/z: 425.1 [MH+].

Example 34

4-Cyano-5-[1-(3-{ethylamino}propyl)-3-indolyl]-1-(1-methyl-3-indolyl)-2,3-dihydroimidazol-2-one trifluoroacetic acid salt $^1$H-NMR (400 MHz, DMSO-d6): δ 1.13 (3H, t, J 7.2 Hz), 1.91 (2H, p, J 7.8 Hz), 2.61–2.70 (2H, m), 2.81 (2H, hept, J 6.4 Hz), 3.77 (3H, s), 4.20 (2H, t, J 7.0 Hz), 6.94 (1H, t, J 7.5 Hz), 7.03 (1H, t, J 7.5 Hz), 7.10–7.20 (3H, m), 7.44 (1H, d, J 8.2 Hz), 7.46 (1H, d, J 7.8 Hz), 7.49 (1H, s), 7.51 (1H, d), 7.60 (1H, s), 8.20 (2H, bs), 11.43 (1H, s).

FAB-MS m/z: 439.1 [MH+].

Example 35

5-[1-(2-Aminomethyl-3-methylbutyl)-3-indolyl]-4-cyano-1-(1-methyl-3-indolyl)-2,3-dihydroimidazol-2-one hydrochloride $^1$H-NMR (400, MHz, CD$_3$OD): δ 0.67 (3H, d, J 7.0 Hz), 0.71 (3H, d, J 7.0 Hz), 1.15 (1H, m), 2.02 (1H, m), 2.54 (1H, dd, J 7.3, 13.3 Hz), 2.87 (1H, dd, J 5.9, 13.3 Hz), 3.73 (3H, s), 4.01 (1H, dd, J 8.6, 14.7 Hz), 4.11 (1H, dd, J 6.7, 14.7 Hz), 6.94 (1H, bt, J 7.2 Hz), 7.08 (1H, bt, J 7.2 Hz), 7.15 (2H, m), 7.17 (1H, s), 7.20 (1H, bt, J 7.7 Hz), 7.34 (1H, s) 7.35 (1H, d, J 8.3 Hz), 7.40 (1H, d, J 8.3 Hz), 7.54 (1H, d, J 8.3 Hz).

LC/APCI-MS m/z: 453 [MH+].

Example 36

4-Cyano-1-(1-methyl-3-indolyl)-5-[1-(3-{1-piperazinyl}propyl)-3-indolyl]-2,3-dihydroimidazol-2-one dihydrochloride a) 4-Cyano-3-(2,4-dimethoxybenzyl)-1-(1-methyl-3-indolyl)-5-{1-[3-(1-piperazinyl)-propyl]-3-indolyl}-3-indolyl]-2,3-dihydroimidazol-2-one The product from Example 17c) (52 mg, 0.08 mmol) and piperazine (100 mg, 1.16 mmol) were stirred in dry THF (1 ml) at 65° C. over night. The solvent and excess amine were removed in vacuum to give the sub-tide compound as a amorphous solid.

APCI-MS m/z: 630 [MH+].

b) 4-Cyano-1-(1-methyl-3-indolyl)-5-[1-{3-(1-piperazinyl)propyl]-3-indolyl}]-2,3-dihydroimidazol-2-one The crude product from step a) (0.08 mmol) and triflic acid (0.07 ml, 0.8 mmol) were stirred in acetonitrile (2 ml) at 65° C. for 3.5 hours. Saturated NaHCO3(aq) was added and the product extracted with ethyl acetate. The organic phase was washed with water, brine, dried and evaporated. The residue was purified by silica gel chromatography (dichloromethane-methanol, 15:1, dichloromethane-methanol-ammoniumhydroxide (25%), 90:10:1) to give 17 mg (44%) of the sub-title compound.

APCI-MS m/z: 480 [MH+].

The product from step b) (17 mg, 0.035 mmol) was dissolved in acetonitrile-HCl(aq) (0.2 M) (1:1, 10 ml), diluted with water (40 ml) and lyophilized to give 16 mg (84%) of the title compound.

$^1$H-NMR (400 MHz, DMSO-d6): δ 11.82 (1H, bs), 11.41 (1H, s,), 9.40 (2H, bs), 7.57 (1H, s), 7.52–7.40 (4H, m), 7.17–7.09 (3H), 7.02 (1H, bt), 6.93 (1H, bt), 4.18 (2H, m), 3.95–2.80 (10H, m), 3.76 (3H, s), 2.07–1.90 (2H, m).

FAB-MS m/z: 480 [MH+].

Example 37

4-Cyano-1-(1-methyl-3-indolyl)-5-{1-[3-(4-morpholinyl)propyl]-3-indolyl}-2,3-dihydroimidazol-2-one hydrochloride The title compound was prepared according to the procedure of Example 36, starting from the product of Example 17c) and morpholine.

$^1$H-NMR (400 MHz, DMSO-d6): δ 11.41 (1H, s), 10.58 (1H, bs), 7.59 (1H, s), 7.52–7.41 (4H, m), 7.18–7.09 (3H, m), 7.02 (1H, bt), 6.93 (1H, bt), 4.20 (2H, bt), 3.96–3.90 (2H, m), 3.75 (3H, s), 3.75–3.69 (2H, m), 3.33–3.24 (2H, m), 2.94–2.84 (4H, m), 2.05–1.95 (2H, m).

FAB-MS m/z: 481 [MH+].

Example 38

4-Cyano-5-{1-[3-(1-imidazolyl)propyl]-3-indolyl}-1-(1-methyl-3-indolyl)-2,3-dihydroimidazol-2-one trifluoroacetic acid salt a) 4-Cyano-3-(2,4-dimethoxybenzyl)-1-5-{1-[3-(1-imidazolyl)-propyl]-3-indolyl}-1-(1-methyl-3-indolyl)-(1-methyl-3-indolyl)-2,3-dihydroimidazol-2-one Sodium hydride (7 mg, 0.164 mmol) and imidazole (11 mg, 0.162 mmol) was stirred in dry DMF (1 ml) at room temperature for 0.5 hours. The product from Example 17c) (100 mg, 0.156 mmol) in dry dimethylformamide (3 ml) was added and the mixture was stirred at 75° C. for 8 hours, poured into water and extracted with ethyl acetate. The organic phase was washed with water, brine, dried and evaporated. The residue was purified by silica gel chromatography (dichloromethane:methanol, 13:1) to give 69 mg (72%) of the sub-title compound.

$^1$H-NMR (400 MHz, CDCl$_3$): δ 7.62 (1H, d, J 8.0 Hz), 7.52 (1H, s), 7.43 (1H, d, J 8.0 Hz), 7.28 (1H, s), 7.26–7.15 (4H, m), 7.08–7.03 (3H), 6.89–6.85 (2H, m), 6.58 (1H, s), 6.53–6.48 (2H, m), 3.93 (3H, s), 3.89 (2H, bt, J 6.1 Hz), 3.82 (3H, s), 3.71 (3H, s), 3.23 (2H, bt, J 6.8 Hz), 2.02 (2H, m).

APCI-MS m/z: 612 [MH+].

Triflic acid (0.07 ml, 0.79 mmol) was added to the compound from step a) (65 mg, 0.11 mmol) in acetonitrile (4 ml). The mixture was stirred at 65° C. after 4 hours more triflic acid (0.07 ml, 0.79 mmol) was added and the mixture was stirred at 65° C. for another 6 hours. Ethyl acetate was added and the organic phase was washed with saturated aqueous sodium hydrogencarbonate, water, brine, dried and evaporated. The residue was purified by C18-reversed phase chromatography (methanol-water-trifluoroacetic acid, 70:30:0.1) and lyophilized to give 35 mg (57%) of the tide compound.

¹H-NMR (400 MHz, CD₃OD): δ 8.46 (1H, bs), 7.55 (1H, bd, J 8.0 Hz), 7.36–7.34 (2H), 7.30 (1H, bd, J 8.2 Hz), 7.22 (1H, bd, J 8.4 Hz), 7.21–7.15 (2H), 7.12 (1H, s), 7.11–7.06 (2H), 6.96 (1H, bt), 6.86 (1H, bt), 4.07 (2H, bt, J 6.5 Hz), 3.70 (3H, s), 3.52 (2H, bt, J 7.4 Hz), 2.09 (2H, m).

FAB-MS m/z: 462 [MH+].

Example 39

5-[1-(3-Bromopropyl)-3-indolyl]-4-cyano-1-(1-methyl-3-indolyl)-2,3-dihydroimidazol-2-one a) 4-Cyano-3-(2,4-dimethoxybenzyl)-1-(1-methyl-3-indolyl)-5-[1-(3-bromopropyl)-3-indolyl]-2,3-dihydroinidazol-2-one 1,3-Dibromopropane (2.30 ml, 22.67 mmol) was added to 4-cyano-3-(2,4-dimethoxybenzyl)-5-(3-indolyl)-1-(1-methyl-3-indolyl)-2,3-dihydroimidazol-2-one (1.849 g, 3.67 mmol) and potassium carbonate (2.78 g, 20.0 mmol) in DMF (10.0 ml). The slurry was stirred at 45° C. for 16 hours, then diluted with ethyl acetate (50 ml) and washed with water (200 ml+100 ml). Some ethyl acetate and 5% NaCl (aq) was added in the last washing step. The solvent was evaporated and the excess 1,3-dibromopropane was removed in a kugelrhor apparatus (0.3 torr, 100° C.) for 20 minutes. Chromatography of the residue (gradient ethyl acetate:heptane from 50:50 to 70:30) afforded 1.84 g of the title compound (80%) as a yellow oil.

¹H-NMR (400 MHz, CD₃OD): δ 7.65 (1H, s), 7.50 (2H, t, J 8.6 Hz), 7.44 (1H, d, J 8.6 Hz), 7.28 (1H, s), 7.21–7.04 (5H, m), 6.90 (1H, t, J 7.6 Hz), 6.67 (1H, d, J 2.5 Hz), 6.60 (1H, dd, J 8.4, 2.5) Hz); 4.90 (2H, s), 4.18 (2H, t, J 6.4 Hz), 3.89 (3H, s), 3.81 (3H, s, OCH₃), 3.79 (3H, s), 2.83 (2H, t, J 6.6 Hz), 2.0 (2H, p, J 6.6 Hz).

APCI-MS m/z: 624/626.0 [MH+].

Triflic acid (0.3 ml, 3.4 mmol) was added to the product from step a) (1.83 g, 2.9 mmol) in acetonitrile (100 ml). The mixture was stirred at 70° C. for 3 hours and concentrated to approx. 50 ml. The slurry was poured into saturated NaHCO3(aq) and extracted with dichloromethane. The organic phase was dried and evaporated and the residue in bezene:ethyl acetate (1:1, 20 ml) was warmed to reflux and stirred at room temperature over night. The precipitate was filtered and washed with ethyl acetate to give 0.95 g (69%) of the title compound.

¹H-NMR (400 MHz, DMSO-d6): δ 11.39 (1H, bs), 7.58 (1H, s), 7.55 (1H, d, J 8.0 Hz), 7.46 (1H, d, J 8.2 Hz), 7.41 (1H, d, J 8.4 Hz), 7.37 (1H, s), 7.23 (1H, s), 7.17 (1H, bt), 7.12–7.03 (2H), 6.87 (1H, bt), 4.16 (2H, bt, J 6.2 Hz), 3.77 (3H, s), 2.80 (2H, bt, J 6.6 Hz), 1.98 (2H, m).

APCI-MS m/z: 475 [MH+].

Example 40

5-{1-[3-(2-Aminoethylamino)propyl]-3-indolyl}-4-cyano-1-(1-methyl-3-indolyl)-2,3-dihydroimidazol-2-one trifluoroacetic acid salt Ethylenediamine (0.13 ml, 1.9 mmol) was added to a slurry of the compound obtained from Example 39 (30 mg, 0.063 mmol) in dry THF (1 ml). The mixture was stirred at 65° C. over night and evaporated. The residue was purified by C18-reversed phase chromatography (methanol-water-trifluoroacetic acid, 60:40:0.1) and lyophilized to give 20 mg (46%) of the title compound.

¹H-NMR (500 MHz, DMSO-d6): δ 11.41 (1H, bs), 8.67 (2H, bs), 7.94 (3H, bs), 7.57 (1H, s), 7.50–7.40 (4H, m), 7.17–7.10 (3H, m), 7.01 (1H, bt), 6.92 (1H, bt), 4.18 (2H, bt, J 6.9 Hz), 3.74 (3H, s), 3.04 (4H, m), 2.77 (2H, m), 1.91 (2H, m).

FAB-MS m/z: 454 [MH+].

The following compounds were made according to the procedure of Example 40, starting from the product of Example 39 and reacted with the appropriate amine.

Example 41

5-{1-[3-({4-Aminobutyl}amino)propyl]-3-indolyl}-4-cyano-1-(1-methyl-3-indolyl)-2,3-dihydroimidazol-2-one trifluoroacetic acid salt ¹H-NMR (500 MHz, DMSO-d6): δ 11.42 (1H, bs), 8.51 (2H, bs), 7.80 (3H, bs), 7.58 (1H, s), 7.50–7.40 (4H, m), 7.17–7.09 (3H, m), 7.01 (1H, bt), 6.92 (1H, bt), 4.19 (2H, bt), 3.74 (3H, s), 2.77 (4H, m), 2.67 (2H, m), 1.92 (2H, m), 1.55 (4H, m).

FAB-MS m/z: 482 [MH+].

Example 42

4-Cyano-5-{1-[3-({2-hydroxyethyl}amino)-propyl]-3-indolyl}-1-(1-methyl-3-indolyl)-2,3-dihydroimidazol-2-one hydrochloride ¹H-NMR (400 MHz, CD₃OD): δ 7.44(1H, d, J 7.4 Hz), 7.42 (1H, d, J 8.1 Hz), 7.38 (1H, d, J 8.3 Hz), 7.35 (1H, s), 7.31 (1H, s), 7.22–7.15 (3H, m), 7.03 (1H, t, J 8.0 Hz), 6.98 (1H), 4.22 (2H, t, J 6.2 Hz), 3.76 (3H, s), 3.72 (2H, m), 2.93 (2H, t, J 5.2 Hz), 2.73 (2H, m), 2.06 (2H, m).

FAB-MS m/z: 455.2 [MH+].

Example 43

5-{1-[3-[({Benzo[1,3]dioxol-5-yl}methyl)-amino]propyl]-3-indolyl}-4-cyano-1-(1-methyl-3-indolyl)-2,3-dihydroimidazol-2-one hydrochloride ¹H-NMR (400 MHz, CDCl₃): δ 7.43 (1H, d, J 8.2 Hz), 7.39 (1H, d, J 8.2 Hz), 7.36 (1H, d, J 8.2 Hz), 7.34 (1H, s), 7.30 (1H, s), 7.21 (2H, t, J 7.7 Hz), 7.16 (1H, t, J 6.9 Hz), 7.03 (1H, t, J 7.5 Hz), 6.99 (1H, t, J 7.5 Hz), 6.87 (1H, s), 6.81 (2H, s), 5.99 (2H, s), 4.20 (2H, t, J 6.6 Hz), 3.89 (2H, s), 3.74 (3H, s), 2.73 (2H, m), 2.05 (2H, m).

FAB-MS m/z: 545.3 [MH+].

Example 44

4-Cyano-1-(1-methyl-3-indolyl)-5-[1-[3-({3-propargyl}amino]-propyl)-3-indolyl]-2,3-dihydroimidazol-2-one hydrochloride ¹H-NMR (400 MHz, CD₃OD): δ 7.46 (1H, d, J 8.0 Hz), 7.42 (1H, d, J 8.2 Hz), 7.38 (1H, d, J 8.2 Hz), 7.35 (1H, s), 7.29 (1H, s), 7.20–7.19 (2H, m), 7.17 (1H, t, J 7.5 Hz), 7.04 (1H, t, J 7.5 Hz), 6.98 (1H, t, J 7.2 Hz), 4.21 (2H, t, J 6.8 Hz), 3.76 (5H, s), 3.18 (1H, t, J 2.6 Hz), 2.82–2.78 (2H, m), 2.07–2.00 (2H, m).

FAB-MS m/z: 449.1 [MH+].

Example 45

4-Cyano-1-(1-methyl-3-indolyl)-5-[1-(3-[{3-pyridyl}methylamino]propyl)-3-indoyl]-2,3-dihydroimidazol-2-one dihydrochloride ¹H-NMR (400 MHz, CD₃OD): δ 8.74 (1H, s), 8.71 (1H, s), 8.12 (1H, d, J 8.1 Hz), 7.67 (1H, dd, J 8.1, 2.9) Hz), 7.42

(2H, d, J 8.3 Hz), 7.37 (1H, d, J 8.5 Hz), 7.37 (1H, s), 7.36 (1H, s), 7.23 (1H, d, J 7.4 Hz), 7.20 (1H, t, J 7.4 Hz), 7.16 (1H, t, J 7.4 Hz), 7.04–6.98 (2H, m), 4.25 (2H, t, J 6.7 Hz), 4.17 (2H, s), 3.75 (3H, s), 2.89–2.86 (2H, m), 2.16–2.08 (2H, m).

FAB-MS m/z: 502.1 [MH+].

Example 46

4-Cyano-5-[1-{3-([2-hydoxyethoxy]ethylamino)propyl}-3-indolyl]-1-(1-methyl-3-indolyl)-3-indolyl]-2,3-dihydroimidazol-2-one hydrochloride $^1$H-NMR (400 MHz, CD$_3$OD): δ 7.44 (2H, t, J 8.5 Hz), 7.38 (1H, d, J 8.5 Hz), 7.36 (1H, s), 7.31 (1H, s), 7.22–7.15 (3H, m), 7.04 (1H, t, J 7.5 Hz), 6.98 (1H, t, J 7.5 Hz), 4.22 (2H, t, J 6.9 Hz), 3.76 (3H, s), 3.70–3.64 (2H, m), 3.56–3.54 (2H, m), 3.02 (2H, t, J 5.0 Hz), 2.74–2.70 (2H, m), 2.09–2.02 (2H, m).

FAB-MS m/z: 499.1 [MH+].

Example 47

4-Cyano-1-(1-methyl-3-indolyl)-5-[1-(3-(2,2,2-trifluoroethylamino)propyl)-3-indolyl]-2,3-dihydroimidazol-2-one hydrochloride $^1$H-NMR (400 MHz, CD$_3$OD): δ 7.43 (1H, d, J 8.6 Hz), 7.43 (1H, d, J 8.6 Hz), 7.37 (1H, d, J 8.1 Hz), 7.34 (1H, s), 7.33 (1H, s), 7.23 (1H, d, J 7.5 Hz), 7.20 (1H, t, J 7.5 Hz), 7.16 (1H, t, J 7.5 Hz), 7.02 (1H, t, J 7.5 Hz), 6.99 (1H, t, J 7.5 Hz), 4.22 (2H, t, J 6.6 Hz), 3.83 (2H, q, J 9.4 Hz), 3.74 (3H, s), 2.99–2.86 (2H, m), 2.15–2.08 (2H, m).

FAB-MS m/z: 493.0 [MH+]

Example 48

4-Cyano-5-[1-(3-cyanopropyl)-3-indolyl]-1-(1-methyl-3-indolyl)-2,3-dihydroimidazol-2-one Prepared in analogy with the examples above, by reacting the product from Example 39 with sodium cyanide.

$^1$HNMR (400 MHz, DMSO-d6): δ 11.41 (1H, s), 7.61 (1H, d, J 7.9 Hz), 7.55 (1H, d, J 8.3 Hz), 7.48 (1H, d, J 8.3 Hz), 7.44 (1H, s), 7.19 (1H, t, J 7.8 Hz), 7.11 (1H, t, J 7.8 Hz), 7.09 (1H, t, J 7.8 Hz), 7.04 (1H, d, J 7.9 Hz), 6.88 (1H, t, J 7.9 Hz), 4.13 (2H, t, J 5.9 Hz), 3.79 (3H, s), 1.81–1.73 (4H, m).

FAB-MS m/z: 421.2 [MH+]

Example 49 cis-5-[1-(4-Aminocyclohexyl)-3-indolyl]-4-cyano-1-(1-methyl-3-indolyl)-2,3-dihydroimidazol-2-one a) 5-{1-[(1S,4R)-4-(tert-Butyldimethylsilanyloxy)-2-cyclohexenyl]-3-indolyl}-4-cyano-3-(2,4-dimethoxybenzyl)-1-(1-methyl-3-indolyl)-2,3-dihydroimidazol-2-one In a flask was added 0.30 g (0.59 mmole) of the product obtained in Example 17 step b), 0.012 g (1.5 mmole) of lithium hydride and 5 ml of dry DMF. The mixture was stirred under nitrogen at 60° C. for 45 min. The solution was degassed, and a solution of 0.16 g (0.59 mmole) of (1S,4R)-1-Acetoxy-4-(tert-butyldimethylsilanyloxy)-2-cyclohexene, 0.030 g (0.033 mmole) of Pd$_2$(dba)$_3$, 0.046 g (0.17 mmole) of triphenylphosphine, 2 mg of lithium chloride in 5 ml of DMF was added rapidly. The resulting solution was degassed again and stirred at 70° C. for 90 minutes. The solution was partitioned between ethyl acetate and water. The organic phase was collected and concentrated. The residue was purified on silica (Heptane:EtOAc 3:2) giving 0.36 g (85%) of the subtitle compound.

$^1$H-NMR (400 MHz, CDCl$_3$): δ 0.12 (6H, d, J 6.6 Hz), 0.96 (9H, s), 1.28–1.40 (1H, m), 1.58–1.69 (1H, m), 1.74–1.84 (1H, m), 1.85–1.92 (1H, m), 3.73 (3H, s), 3.84 (3H, s), 3.95 (3H, s), 4.13–4.20 (1H, m), 4.65–4.72 (1H, m), 5.05 (2H, s), 5.32 (1H, dd, J 10.5, 2.5 Hz), 5.86 (1H, dt, J 9.7, 2.4 Hz), 6.49–6.54 (2H, m), 6.93 (1H, t, J 7.5 Hz), 6.99 (1H, bs), 7.09–7.21 (5H, m), 7.25 (1H, d, J 8.3 Hz), 7.35 (1H, d, J 8.2 Hz), 7.44 (1H, d, 8.2 Hz), 7.57 (1H, d, J 8.1 Hz).

FAB-MS m/z: 714.3 [MH+].

b) 5-{1-[(1S,4R)-4-Acetoxy-2-cyclohexenyl]-3-indolyl}-4-cyano-3-(2,4-dimethoxybenzyl)-1-(1-methyl-3-indolyl)-2,3-dihydroimidazol-2-one In a flask was dissolved 0.11 g (0.15 mmole) of the product from step a) in 10 ml of THF. To this solution was added 0.145 g (0.46 mmole) of tetrabutylammonium fluoride. The solution was stirred for 30 minutes. After this, 0.20 g (1.9 mmole) of acetic anhydride and 0.156 g (1.9 mmole) of pyridine was added and the resulting solution stirred for 90 minutes. The solution was concentrated in vaccuo, the crude product was purified on silica (Heptane:EtOAc 2:3) to give 0.095 g (96%) of the sub-title compound as a white solid.

$^1$H-NMR (400 MHz, CDCl$_3$): δ 1.47–1.53 (1H, m), 1.76–1.83 (2H, m), 1.86–1.93 (1H, m), 2.14 (3H, s), 3.73 (3H, s), 3.84 (3H, s), 3.95 (3H, s), 4.75–4.82 (1H, m), 5.05 (2H, s), 5.18–5.25 (1H, m), 5.56 (1H, dd, J 10.2, 2.7 Hz), 5.91 (1H, dt, J 10.1, 2.4 Hz), 6.48–6.54 (2H, m), 6.96 (1H, t, J 8.0 Hz), 6.99 (1H, s), 7.10–7.22 (5H, m), 7.24 (1H, t, J 7.5 Hz), 7.28–7.32 (1H, m), 7.44 (1H, d, J 8.0 Hz), 7.55 (1H, d, J 8.0 Hz)

FAB-MS m/z: 642.4 [MH+].

c) 4-Cyano-5-{1-[(1S,4R)-4-(1,3-dihydroisoindol-2-yl)-2-cyclohexenyl]-3-indolyl}-3-(2,4-dimethoxybenzyl)-1-(1-methyl-3-indolyl)-2,3-dihydroimidazol-2-one In a flask was added 0.064 g (0.10 mmole) of the product obtained in step b), 0.046 g (0.25 mmole) of potassium phthalimide, 0.0096 g (0.01 mmole) of Pd$_2$(dba)$_3$, 0.013 g (0.05 mmole) of triphenylphosphine, 1 mg of lithium chloride and finally 7 ml of dry DMF. The flask was sealed and stirred under nitrogen at 70° C. under nitrogen for 90 minutes. The mixture was partitioned between EtOAc and water, and the organic phase was collected and concentrated. The residue was purified on silica (Heptane:EtOAc 1:3), giving 0.040 g (55%) of the sub-title compound as a white solid.

$^1$H-NMR (400 MHz, CDCl$_3$) δ 1.51–1.67 (2H, m), 1.78–1.89 (1H, m), 1.94–2.05 (1H, m), 3.59 (3H, s), 3.85 (3H, s), 3.97 (3H, s), 4.80–4.87 (1H, m), 4.88–4.93 (1H, m), 5.08 (2H, d, J 2.5 Hz), 5.57 (1H, d, J 10.0 Hz), 5.91 (1H, d, J 10.0 Hz), 6.51–6.56 (2H, m), 6.76 (1H, t, J 7.7 Hz), 6.98–7.04 (2H, m), 7.12 (1H, d, J 10.0 Hz), 7.17 (1H, t, J 7.3 Hz), 7.23 (1H, t, J 7.2 Hz), 7.32 (1H, d, J 8.2 Hz), 7.45–7.50 (2H, m), 7.63 (1H, d, J 8.0 Hz), 7.71 (1H, s), 7.80–7.83 (2H, m), 7.91–7.94 (2H, m).

APCI-MS m/z: 729.0 [MH+].

d) cis-4-Cyano-3-(2,4-dimethoxybenzyl)-5-{1-[4-(1,3-dioxo-1,3-dihydroisoindol-2-yl)-cyclohexyl]-3-indolyl}-1-(1-methyl-3-indolyl)-2,3-dihydroimidazol-2-one In a flask was dissolved 0.040 g (0.055 mmole) of the product obtained in step c), 0.015 g of 5% Pd(C) in 3 ml of ethyl acetate and 3 ml of ethanol. The substance was hydrogenated at normal pressure and 25° C. for 72 hours. The solution was filtered and evaporated to give the sub-title compound as a white solid. The product was used in the next step without further purification.

FAB-MS m/z: 731.2 [MH+].

In a flask was added of the product obtained in step d) (0.030 g, 0.041 mmole), acetonitrile (10 ml) and 5 drops of triflic acid. The flask was sealed and stirred at 70° C. for 3 h. To the mixture was then added 2 ml of triethyl amine and the solvent was evaporated. The residue was dissolved in 5 ml of THF and 1 ml of 40% MeNH$_2$(aq) was added. The mixture was stirred for 2 hours, the solvent evaporated andthe residue purified by preparative HPLC, and lyophilized to give 0.007 g (30%) of the title compound as a white solid.

FAB-MS m/z: 451.1 [MH+].

Example 50

5-[1-(4-Aminobutyl)-3-indolyl]-4-cyano-3-methyl-1-(1-propyl-3-indolyl)-2,3-dihydroimidazol-2-one a) 4-Cyano-5-{1-[4-(1,3-dioxo-1,3-dihydroisoindol-2-yl)-butyl]-3-indolyl}-3-methyl-1-(1-propyl-3-indolyl)-2,3-dihydroimidazol-2-one In a flask was added 0.055 (0.095 mmole) of the product obtained from Example 9f), methyliodide 0.050 g (0.35 mmole), 0.045 g (0.14 mmole) of Cs$_2$CO$_3$, in 1 ml of DMF. The flask was sealed and stirred at 50° C. for 3 hours. The product mixture was partitioned between ethyl acetate and water. The organic phase was collected and concentrated, giving the sub-title compound as a crude, which was used futher without purification.

APCI-MS m/z: 597.1 [MH+].

The product obtained in step a) was dissolved in 20 ml of THF, and 5 ml of 40% MeNH$_2$(aq) was added. The mixture was stirred for 3 hours, and the solvent evaporated. The residue was purified on preparative HPLC, giving 0.029 g (53%) of the title compound as a white solid.

$^1$H-NMR (400 MHz, DMSO-d6): δ 0.64 (3H, t, J 7.6 Hz), 1.28 (2H, d, J 7.5 Hz), 1.53–1.67 (4H, m), 2.61–2.71 (2H, m), 3.37 (3H, s), 4.02–4.12 (4H, m), 6.90 (1H, t, J 7.6 Hz), 6.95 (1H, t, J 7.6 Hz), 7.05–7.15 (3H, m), 7.37–7.41 (2H, m), 7.44 (2H, d, J 8.5 Hz), 7.55 (1H, s), 7.60 (3H, bs).

FAB-MS m/z: 467.1 [MH+].

Example 51

4-Cyano-5-{1-[3-(guanidinomethyl)benzyl]-3-indolyl}-1-(1-methyl-3-indolyl)-2,3-dihydroimidazol-2-one trifluoroacetic acid salt.

78 mg (0.13 mmol) of the title compound from Example 8 and 52 mg (0.16 mmol) of benzotriazole-1-carboxamidinium tosylate were dissolved in 0.2 ml of DMF. 50 μl (0.29 mmol) of diisopropylethylamine was added. The reaction was stirred at room temperature over night. The crude was purified by preparative HPLC. Yield 46 mg, (56%).

$^1$H-NMR (400 MHz, DMSO-d6): δ 3.74 (3H, s), 4.26 (2H, d, J 4.8 Hz), 5.30 (2H, s), 6.42 (1H, bs), 6.92 (1H, t, J 8.0 Hz), 7.02 (1H, t, J 7.6 Hz), 7.18–7.06 (6H, m), 7.36 (1H, d, J 8.0 Hz), 7.44 (1H, d, J 8.0 Hz), 7.52–7.49 (2H, m), 7.58 (1H, s), 11.40 (1H, bs).

FAB-MS m/z: 515.2 [MH+].

Example 52

4-Cyano-1-(1-methyl-3-indolyl)-5-[1-((2S)-2-pyrrolidine-carbonyl)-3-indolyl]-2,3-dihydroimidazol-2-one trifluoroacetic acid salt a) 4-Cyano-3-(2,4-dimethoxybenzyl)-1-(1-methyl-3-indolyl)-5-{1-[((2S)-2-pyrrolidine-1-tert-butoxycarbonyl)-carbonyl]-3-indolyl}-2,3-dihydroimidazol-2-one A portion of 100 mg (0.20 mmol) of the title compound from Example 17b) and 86 mg (0.40 mmol) of N-Boc-L-proline were dissolved in DMF. 165 mg (0.44 mmol) of O-(benzotriazol-1-yl)-N,N,N',N'-tretrauronium hexafluorophosphate, 165 mg (0.20 mmol) of 1-hydroxybenzotriazole and 150 μl (0.88 mmol) of diisopropylethylamine were added. The reaction was stirred over night. Ethyl acetate was added and the organic phase was washed with 5% KHSO$_4$(aq) and 5% NaHCO$_3$(aq) and dried over Na$_2$SO$_4$, the product was used without further purification.

The crude product from step a) was dissolved in 10 ml acetonitrile. 150 μl of Tioanisol and 370 μl of trifluoromethanesulfonic acid were added. The glass-vessel was sealed and the reaction stirred at 70° C. for 4 hours, cooled to room temperature and neutralized by adding sodium acetate. The product was purified by preparative HPLC to give 73 mg (65%) of the title compound.

$^1$H-NMR (400 MHz, DMSO-d6): 1.58–1.43 (1H, m), 1.87–1.68 (2H, m), 2.03–1.87 (1H, m), 3.23–2.95 (2H, m), 3.74 (3H, s), 4.92–4.67 (1H, m), 6.97 (1H, t, J 8 Hz), 7.13 (1H, t, J 8 Hz), 7.31–7.22 (2H, m), 7.45–7.33 (2H, m), 7.59 (1H, d, J 8 Hz), 7.64 (1H, s), 8.03 (1H, s), 8.25 (1H, d, J 8 Hz).

FAB-MS m/z: 451.1 [MH].

Example 53

4-Cyano-1-(1-methyl-3-indolyl)-5-[1-((2R)-2-pyrrolidine-carbonyl)-3-indolyl]-2,3-dihydroimidazol-2-one trifluoroacetic acid salt.

a) 4-Cyano-3-(2,4-dimethoxybenzyl)-1-(1-methyl-3-indolyl)-5-{1-[(2R-pyrrolidine-1-tert-butoxycarbonyl]-carbonyl}-3-indolyl]-2,3-dihydroimidazol-2-one A portion of 86 mg (0.40 mmol) of N-Boc-D-proline and 100 mg (0.20 mmol) of the title compound from Example 17b) were dissolved in DMF. A portion of 165 mg (0.44 mmol) of O-(benzotriazol-1-yl)-N,N,N',N'-tretrauronium hexafluorophosphate, 165 mg (0.20 mmol) of 1-hydroxybenzotriazole and 150 μl (0.88 mmol) of diisopropylethylamine were added. The reaction was stirred over night. Ethyl acetate was added and the organic phase was washed with 5% KHSO$_4$(aq) and 5% NaHCO$_3$(aq) and dried over Na$_2$SO$_4$, the product was used without further purification.

The crude product from step a) was dissolved in 10 ml of acetonitrile. 150 μl of tioanisol and 370 μl of trifluoromethanesulfonic acid were added. The glass-vessel was sealed and the reaction was stirred at 70° C. for 4 hours, cooled to room temperature and neutralized by addition of sodium acetate, neat. The product was purified by preparative HPLC to give 58 mg (51%) of the title compound.

$^1$H-NMR (400 MHz, DMSO-d6) δ 1.54–1.44 (1H, m), 1.79–1.70 (2H, m), 1.93–1.83 (1H, m), 3.12–2.98 (2H, m), 3.74 (3H, s), 4.72–4.62 (1H, m), 6.97 (1H, t, J 8 Hz), 7.14 (1H, t, J 8 Hz), 7.25 (1H, d, J 8 Hz), 7.29 (1H, d, J 8 Hz), 7.37 (1H, t, J 8 Hz), 7.43 (1H, d, J 8 Hz), 7.59 (1H, d, J 8 Hz), 7.64 (1H, s), 8.01 (1H, s), 8.25 (1H, d, J 8 Hz).

FAB-MS m/z: 451.1 [MH+].

Example 54

4-Cyano-1-(1-methyl-3-indolyl)-5-{1-[(1S,3R)-1-(3-toluene-4-sulfonylamino)-cyclopentyl-methyl]-3-indolyl}-2,3-dihydroimidazol-2-one a) (R)-Methanesulfonic acid [{4S-(toluene-4-sulfonylamino)-2-cyclopentenyl}methyl]ester In a nitrogen filled reaction vessel 1.4 g (5.26 mmol) of crude N-(4-Hydroxymethyl-cyclopent-2-enyl)-4-methylbenzenesulfonamide was dissolved in dry dichloromethane. 0.99 g (5.66 mmol) of methansulfonic anhydride and 1.67 ml (20.7 mmol) of pyridine were added at room temperature. After 4 hours the reaction mixture was poured into a saturated ammonium chloride solution. The organic layer was collected, washed twice with water and dried over sodium sulfate. The sub-title product was purified by flash-chromatography (Heptane:EtOAc 1:1) to give 0.38 g (21%) of the sub-title compound.

APCI-MS m/z: 346 [MH+].

b) 4-Cyano-3-(2,4-dimethoxybenzyl)-1-(1-methyl-3-indolyl)-5-{1-[(1S,3R)-3-(toluene-4-sulfonylamino)-2-cyclopentenyl}-methyl]-3-indolyl}-2,3-dihydroimidazol-2-one A portion of 327 mg (0.65 mmol) of the title compound from Example 17b) was dissolved in 1.0 ml of DMF. 1.1 g (3.24 mmol) of $Cs_2CO_3$ was added and the mixture was stirred for 30 minutes. 224 mg (0.65 mmol) of the product from step a) dissolved in 0.5 ml of DMF was added. The reaction was stirred at 35° C. over night, cooled to room temperature and ethyl acetate and a saturated $NH_4Cl(aq)$ solution was added. The organic layer was collected, washed twice with water and dried over sodium sulfate. The crude was used without further purification.

APCI-MS m/z: 753 [MH+]

c) 4-Cyano-3-(2,4-dimethoxybenzyl)-1-(1-methyl-3-indolyl)-5-{1-[(1S,3R)-1-(3-toluene-4-sulfonylamino) cyclopentylmethyl]-3-indolyl}-2,3-dihydroimidazol-2-one A portion of 220 mg of the crude product from step b) was dissolved in 5 ml of a of ethyl acetate:ethanol (1:1). 22 mg of Pd(C) (10%) was added and the reaction was stirred under an atmospheric pressure of hydrogen over night. The catalyst was removed by filtration through celite, and the solvent was evaporated. The crude mixture was used without further purification.

APCI-MS m/z: 755 [MH+].

The crude from step c) was dissolved in 1 ml of acetonitrile. 30 μl of trifluoromethane sulfonic acid was added, and the reaction was heated to 70° C. for 1.5 hours. The reaction was cooled to room temperature and anhydrous sodium acetateadded. The product was purified by preparative HPLC and freeze-dried to give the subtitle product as a white solid.

$^1$H-NMR (500 MHz, $CD_3OD$): δ 0.92–0.78 (2H, m), 1.05–0.95 (1H, m), 1.26–1.18 (1H, m), 1.52–1.38 (2H, m), 1.88–1.80 (1H, m), 2.43 (3H, s), 3.39–3.29 (1H, m), 3.77 (3H, s), 3.92–3.81 (2H, m), 6.91 (1H, t, J 7.5 Hz), 6.94 (1H, s,), 7.18–7.06 (4H, m), 7.29 (1H, d, J 8 Hz), 7.32 (1H, s), 7.34 (1H, d, J 8 Hz), 7.35 (2H, d, J 8 Hz), 7.57 (1H, d, J 8 Hz), 7.70 (2H, d, J 8 Hz).

APCI-MS m/z: 605 [MH+].

Example 55

5-{1-[(1S,3R)-1-(3-Amino)cyclopentlmethyl]-3-indolyl}-4-cyano-1-(1-methyl-3-indolyl)-2,3-dihydroimidazol-2-one trifluoroacetic acid salt a) 5-{1-[(1S,3R)-1-(3-tert-Butoxycarbonyl-amino) cyclopentylmethyl]-3-indolyl}-4-cyano-3-(2,4-dimethoxybenzyl)-1-(1-methyl-3-indolyl)-2,3-dihydroimidazol-2-one A portion of 150 mg of the crude from Example 54c) was dissolved in 0.5 ml of dry THF and stirred with 9.6 mg (0.4 mmol) of sodium hydride for 0.5 hours. 44 mg (0.2 mmol) of $(BOC)_2O$ and 2.4 mg (0.02 mmol) of dimethyl aminopyridine were added, and the reaction was stirred for 1.5 hours at room temperature. The reaction was evaporated. The crude dissolved in ethyl acetate and saturated $NH_4Cl(aq)$. The organic layer was separated, washed twice with a saturated $NH_4Cl(aq)$, once with brine and dried over $Na_2SO_4$. The solvent was evaporated and the crude dissolved in methanol (2.5 ml). Magnesium powder was added and the reaction vessel was sonicated for 2.5 hours. Ethyl acetate and saturated $NH_4Cl(aq)$ were added. The organic layer collected, washed with saturated $NH_4Cl(aq)$ and brine and dried over $Na_2SO_4$. The crude product was used without further purification.

APCI-MS m/z: 701 [MH+].

The crude from step a) dissolved in 5 ml of acetonitrile was treated with 1.1 ml of trifluoromethane sulfonic acid and 60 μl of tioanisole at 70° C. for 4 hours. Sodium acetate was added followed by purification by preparative HPLC to give 3 mg of the title product.

$^1$H-NMR (400 MHz, $CDCl_3$): 1.19–1.04 (3H, m), 1.56–1.46 (1H, m), 2.00–1.82 (2H, m), 2.18–2.06 (1H, m), 3.47–3.39 (1H, m), 3.93 (1H, dd, J 14 Hz, 8 Hz), 4.12 (1H, ddt, J 14 Hz, 6.8 Hz), 6.96 (1H, t, J 7.6 Hz), 7.06 (1H, t, J 7.6 Hz), 7.10 (1H, s), 7.20–7.14 (3H, m), 7.35 (1H, s), 7.38 (1H, d, J 8.4 Hz), 7.38 (1H, d, J 8.8 Hz), 7.53 (1H, d, J 8.0 Hz).

APCI-MS) m/z: 451 [MH+].

Example 56

4-Cyano-1-(1-methyl-3-indolyl)-5-[1-((2R)-2-pyrrolidinylmethyl)-3-indolyl]-2,3-dihydroimidazol-2-one trifluoroacetic acid salt a) 4-Cyano-3-(2,4-dimethoxybenzyl)-1-(1-methyl-3-indolyl)-5-[1-((2R)-1-tert-butoxycarbonyl-2-pyrrolidinylmethyl)-3-indolyl]-2,3-dihydroimidazol-2-one 4-Cyano-3-(2,4-dimethoxybenzyl)-5-(3-indolyl)-1-(1-methyl-3-indolyl)-2,3-dihydroimidazol-2-one (50 mg, 0.1 mmol) was dissolved in DMF (2.0 ml). $Cs_2CO_3$ (164 mg, 0.5 mmol) was added. After stirring the mixture for 1 hour, (R)-N-Boc-2-[[(methylsulfonyl)oxy]methyl]-pyrrolidine (140 mg, 0.5 mmol) dissolved in DMF (1.5 ml) was added. The reaction mixture was stirred at room temperature for 6 days. Additional mesylate (50 mg, 0.18 mmol) dissolved in DMF (0.4 ml) was added. Stirring at room temperature was continued for another 5 days. Ethyl acetate and brine was added. The aqueous phase was extracted with ethyl acetate and the combined organic phases were washed with brine, dried over $Na_2SO_4$ and concentrated. The residue was purified by flash chromatography (Heptan:EtOAc 1:2).

APCI-APCI-MSMS m/z: 687 [MH+].

The product from step a) was dissolved in acetonitrile (10 ml) and treated with trifluoromethanesulfonic acid (1.5 ml) at 70° C. for 5 hours. The reaction mixture was diluted with acetonitrile and neutralized by addition of 40% MeNH$_2$(aq). After evaporation, the residue was purified by preparative HPLC(C18-reversed phase, acetonitrile-water-trifluoroacetic acid). The title compound 21 mg (38%) was obtained after lyophilization as a white solid.

$^1$H-NMR (400 MHz, DMSO-d6): δ 1.11–1.23 (1H, m), 1.27–1.39 (1H, m), 1.63–1.86 (2H, m), 3.03–3.23 (2H, m), 3.56–3.69 (1H, m), 4.26 (1H, dd, J 14.6 Hz, 8.1 Hz), 4.44 (1H, dd, J 14.4 Hz, 6.2 Hz), 6.93 (1H, t, J 7.5 Hz), 7.09–7.17 (3H, m), 7.24 (1H, t, J 7.7 Hz), 7.39 (1H, s), 7.45 (1H, d, J 8.2 Hz), 7.56–7.61 (3H, m), 8.73 (1H, bs), 8.91 (1H, bs), 11.45 (1H, s).

FAB-MS m/z: 437.1 [MH+].

Example 57

4-Cyano-5-[(1S,3S)-1-(3-N,N-dimethylaminocyclopentyl)-3-indolyl]-1-(1-methyl-3-indolyl)-2,3-dihydroimidazol-2-one hydrochloride Sodium triacetoxy borohydride (450 mg, 2.1 mmol) was added in two portions during a period of 4 hours to a solution of the product obtained from Example 18 (44 mg, 0.08 mmol) and formaldehyde (0.6 ml of a 37% aqueous solution) in methanol (4.5 ml) and glacial acetic acid (0.5 ml) and the mixture was stirred at room temperature for 6 hours. The reaction mixture was then concentrated to remove most of the methanol and the residue was partitioned between chloroform and saturated NaHCO$_3$(aq). The aqueous phase was back-extraced twice with chloroform and the combined organic extracts was dried over Na$_2$SO$_4$, concentrated and the residue was subjected to flash chromatography (SiO$_2$, dichloromethane-methanol-ammonium hydroxide, 150:15:1.5). The fractions containing the desired product were combined and concentrated. The residue was dissolved in 1% aqueous acetic acid (10 ml) and freeze-dried to afford title compound as the acetic acid salt (34 mg, 75.6%).

The above compound (30 mg, 0.06 mmol) was dissolved in HCl (aq) (1%) (10 ml) and freeze-dried to afford the title compound (25 mg, 87.2%).

$^1$H-NMR (DMSO-d6): δ 11.42 (1H, s), 10.84 (1H, bs), 7.59 (1H, s), 7.50 (2H, d, J 8.4 Hz), 7.46 (1H, d, J 8.4 Hz), 7.30 (1H, s), 7.14–7.19 (3H, m), 7.06 (1H, t, J 7.6 Hz), 6.97 (1H, t, J 7,6 Hz), 5.02 (1H, m), 3.76 (3H, s), 3.38 (1H, m), 2.70 (3H, bs), 2.66 (3H, bs), 2.34 (1H, m), 2.13 (1H, m), 1.82–1.94 (3H, m), 1.57 (m, 1H).

Example 58

5-[1-(4-Aminobutyl)-3-indoyl]-4-cyano-1-(5,6-dichloro-1-methyl-3-indolyl)-2,3-dihydroimidazol-2-one hydrochloride $^1$H-NMR (400 MHz, DMSO-d6): δ 1.33 (m, 2H), 1.64 (m, 2H), 2.71 (bs, 2H), 3.74 (s, 3H), 4.13 (t, 2H, J 7.0 Hz), 7.03 (dt, 1H, J 7.2, 1.0 Hz), 7.15 (dt, 1H, J 7.2, 1.0 Hz), 7.41 (d, 1H, J 8.0 Hz), 7.42 (s, 1H), 7.44 (s, 1H), 7.50 (d, 1H, J 8.2 Hz), 7.65 (s, 1H), 7.78 (bs, 2H), 7.82 (s, 1H), 11.44 (bs, 1H).

FAB-MS m/z: 493.1 [MH+].

What is claimed is:
1. A compound of formula (I)

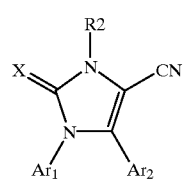

(I)

wherein
Ar$_1$ or Ar$_2$ is an unsubstituted or substituted indole, and the other group is an unsubstituted or substituted aromatic or heteroaromatic group,
X is O or S, and
R2 is hydroxy, amino, C$_{1-6}$alkyl, hydroxyC$_{1-6}$alkyl or aminoC$_{1-6}$alyl, or a salt or a solvate thereof, or a solvate of said salt.

2. A compound of formula (II) or (III)

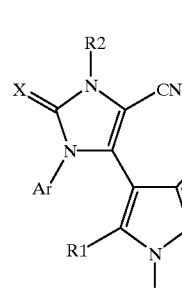

(II)

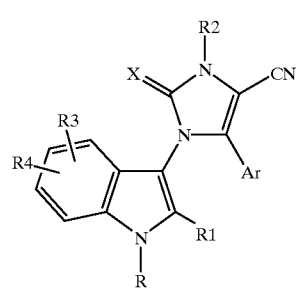

(III)

wherein:
Ar is an unsubstituted or substituted aromatic or heteroaromatic group,
X is O or S,
R is H, C$_{1-6}$alkyl, haloC$_{1-6}$alkyl, benzyl, C$_{1-3}$alkoxy substituted benzyl, nitrileC$_{1-6}$alkyl, hydroxyC$_{1-6}$alkyl, aminoC$_{1-6}$alkyl, (pyridinylmethyl)aminoC$_{1-6}$alkyl, (mono- or di-C$_{1-6}$alkyl)aminoC$_{1-6}$alkyl, (mono- or di-C$_{1-3}$haloalkyl)aminoC$_{1-6}$alkyl, aminoC$_{3-7}$cycloalkyl, (mono- or di-C$_{1-6}$alkyl)amino C$_{3-7}$cycloalkyl, (aminoC$_{3-7}$cycloalkyl)C$_{1-3}$alkyl, (hydroxyC$_{1-6}$alkyl)aminoC$_{1-6}$alkyl, (aminoC$_{1-6}$alkyl)aminoC$_{1-6}$alkyl, (C$_{1-6}$alkynyl)aminoC$_{1-6}$alkyl, (benzyl)aminoC$_{1-6}$alkyl, (mono- or di-C$_{1-3}$alkoxy substituted benzyl)aminoC$_{1-6}$alkyl, (amino C$_{1-3}$alkylphenyl)C$_{1-3}$alkyl, (aminoC$_{1-3}$alkylthiophenyl) C$_{1-3}$alkyl, (aminoC$_{1-3}$alkylpyridinyl) C$_{1-3}$alkylpyridinyl)C$_{1-3}$alkyl, guanidine C$_{1-6}$alkyl, (guanidinoC$_{1-3}$alkylphenyl)C$_{1-3}$alkyl, amidino C$_{1-6}$alkyl or amidinothioC$_{1-6}$alkyl or a group of the formula —Z—(CH$_2$)$_N$-Het in which
Z is carbonyl or methylene
n is an integer of 0–5, and
Het is an unsubstituted or substituted 5- or 6-membered heterocyclic group
R1 is H or C$_{1-3}$alkyl
R2 is H, C$_{1-3}$alkyl, hydroxy, amino, hydroxyC$_{1-3}$alkyl or aminoC$_{1-3}$alkyl
R3 and R4 are each independently H, hydroxy, C$_{1-6}$alkyl, hydroxyC$_{1-6}$alkyl, haloC$_{1-6}$alkyl, C$_{1-3}$alkoxy, carboC$_{1-6}$alkoxy, halogen, nitrile, nitro or amino,
or a salt or a solvate thereof, or a solvate of said salt.

3. A compound according to claim 2, wherein Ar is an unsubstituted or substituted bicyclic aromatic or an unsubstituted or substituted bicyclic heteroaromatic group.

4. A compound according to claim 2, wherein Ar is a heteroaromatic or a bicyclic heteroaromatic group containing a single heteroatom.

5. A compound according to claim 4, wherein the heteroatom is N, O or S.

6. A compound according to claim 2 wherein Ar is selected from benzothiophene, naphthyl, unsubstituted or substituted phenyl or unsubstituted or substituted indolyl.

7. A compound according to claim 2, in which X is O and R2 is H.

8. A compound according to claim 2, in which R is aminoC$_{1-6}$alkyl, (mono- or di-C$_{1-6}$alkyl)aminoC$_{1-4}$alkyl, aminoC$_{3-7}$cycloalkyl, (mono- or di-C$_{1-6}$alkyl)amino-C$_{3-7}$cycloalkyl, (aminoC$_{1-3}$alkylphenyl)C$_{1-3}$alkyl, guanidinoC$_{1-6}$alkyl, amidinoC$_{1-6}$alkyl especially amidinobutyl, amidinothioC$_{1-6}$alkyl, or aminomethyl benzyl.

9. A compound selected from the group consisting of:
5-[1-(3-Aminopropyl)-3-indolyl]-4-cyano-1-(3-indolyl)-2,3-dihydroimidazol-2-one
5-[1-(4-Aminobutyl)-3-indolyl]-4-cyano-1-(3-indolyl)-2,3-dihydroimidazol-2-one
5-[1-(2-Aminoethyl)-3-indolyl]-4-cyano-1-(3-indolyl)-2,3-dihydroimidazol-2-one
5-[1-(3-Aminopropyl)-3-indolyl]-4-cyano-1-(1-methyl-3-indolyl)-2,3-dihydroimidazol-2-one
5-[1-(4-Aminobutyl)-3-indolyl]-4-cyano-1-(1-propyl-3-indolyl)-2,3-dihydroimidazol-2-one
5-[1-(3-Aminopropyl)-3-indolyl]-1-(benzo[b]thiophen-3-yl)-4-cyano-2,3-dihydroimidazol-2-one
5-[1-(3-Amidinothiopropyl)-3-indolyl]-4-cyano-1-(3-indolyl)-2,3-dihydroimidazol-2-one
5-[1-(4-Amidinobutyl)-3-indolyl]-4-cyano-1-(3-indolyl)-2,3-dihydroimidazol-2-one
4-Cyano-5-[1-(3-guanidinopropyl)-3-indolyl]-1-(3-indolyl)-2,3-dihydroimidazol-2-one
5-{1-[3-(Aminomethyl)benzyl]-3-indolyl}-4-cyano-1-(3-indolyl)-2,3-dihydroimidazol-2-one
5-{1-[2-(Aminomethyl)benzyl]-3-indolyl}-4-cyano-1-(1-methyl-3-indolyl)-2,3-dihydroimidazol-2-one
5-{1-[3-(Aminomethyl)benzyl]-3-indolyl}-4-cyano-1-(1-methyl-3-indolyl)-2,3-dihydroimidazol-2-one
5-{1-[4-(Aminomethyl)benzyl]-3-indolyl}-4-cyano-1-(1-methyl-3-indolyl)-2,3-dihydroimidazol-2-one
5-{1-[5-Aminomethyl)-2-thiophenylmethyl]-3-indolyl}-4-cyano-1-(1-methyl-3-indolyl)-2,3-dihydroimidazol-2-one
5-{1-[6-Aminomethyl)-2-pyridylmethyl]-3-indolyl}-4-cyano-1-(1-methyl-3-indolyl)-2,3-dihydroimidazol-2-one
5-[1-[4-Aminobutyl)-3-indolyl]-4-cyano-1-(3-nitrophenyl)-2,3-dihydroimidazol-2-one
4-Cyano-5-[1-(2-(N-isopropylamino)propyl)-3-indolyl]-1-(1-methyl-3-indolyl)-2,3-dihydroimidazol-2-one
4-Cyano-5-[1-(N,N-dimethylaminopropyl)-3-indolyl]-1-(1-methyl-3-indolyl)-2,3-dihydroimidazol-2-one
5-[1-(3-Aminocyclopentyl)-3-indolyl]-4-cyano-(1-methyl-3-indolyl)-2,3-dihihydroimidazol-2-one
4-Cyano-5-[1-(3-hydroxypropyl)-3-indolyl]-1-(3-indolyl)-2,3-dihydroimidazol-2-one
4-Cyano-5-[1-(4-cyanobutyl)-3-indolyl]-1-[1-(ethoxycarbonyl)-3-indolyl]-1,3-dihydroimidazol-2-one
5-[1-(4-Aminobutyl)-3-indolyl]-4-cyano-1-(4-methoxyphenyl)-2,3-dihydroimidazol-2-one
5-[1-(4-Aminobutyl)-3-indolyl]-4-cyano-1-(4-phenoxyphenyl)-2,3-dihydroimidazol-2-one
5-[1-(4-Aminobutyl)-3-indolyl]-1-(4-tert-butylphenyl)-4-cyano-2,3-dihydroimidazol-2-one
5-[1-(4-Aminobutyl)-3-indolyl]-4-cyano-1-[(4-ethoxycarbonyl)phenyl]-2,3-dihydroimidazol-2-one
5-[1-(4-Aminobutyl)-3-indolyl]-4-cyano-1-(1-naphthyl)-2,3-dihydroimidazol-2-one
4-Cyano-5-(3-indolyl)-1-(1-naphthyl)-2,3-dihydroimidazol-2-one
4-Cyano-5-[1-(4-methoxybenzyl)-3-indolyl]-1-(1-methyl-3-indolyl)-2,3-dihydroimidazol-2-one
1-[1-(3-Aminopropyl)-3-indolyl]-4-cyano-5-(1-methyl-3-indolyl)-2,3-dihydroimidazol-2-one
4-Cyano-1-(-3-indolyl)-5-(1-methyl-3-indolyl)-2,3-dihydroimidazol-2-one
4-Cyano-1,5-bis-(1-methyl-3-indolyl)-2,3-dihydroimidazol-2-one
5-[1-(4-Aminobutyl)-3-indolyl]-4-cyano-1-(1-methyl-3-indolyl)-2,3-dihydroimidazol-2-one
4-Cyano-5-[1-(3-{methylamino}propyl)-3-indolyl]-1-(1-methyl-3-indolyl)-2,3-dihydroimidazol-2-one
4-Cyano-5-[1-(3-{ethylamino}propyl)-3-indolyl]-1-(1-methyl-3-indolyl)-2,3-dihydroimidazol-2-one
5-[1-(2-Aminomethyl-3-methylbutyl)-3-indolyl]-4-cyano-1-(1-methyl-3-indolyl)-2,3-dihydroimidazol-2-one
4-Cyano-1-(1-methyl-3-indolyl)-5-[1-(3-{1-piperazinyl}propyl)-3-indolyl]-2,3-dihydroimidazol-2-one
4-Cyano-1-(1-methyl-3-indolyl)-5-{1-[(3-(4-morpholinyl)propyl]-3-indolyl}-2,3-dihydroimidazol-2-one
4-Cyano-5-{1-[3-(1-imidazolyl)propyl]-3-indolyl}-1-(1-methyl-3-indolyl)-2,3-dihydroimidazol-2-one
5-[1-(3-Bromopropyl)-3-indolyl]-4-cyano-1-(1-methyl-3-indolyl)-2,3-dihydroimidazol-2-one
5-{1-[3-(2-Aminoethylamino)propyl]-3-indolyl}-4-cyano-1-(1-methyl-3-indolyl)-2,3-dihydroimidazol-2-one
5-{1-[3-({4-Aminobutyl}amino)propyl]-3-indolyl}-4-cyano-1-(1-methyl-3-indolyl)-2,3-dihydroimidazol-2-one
4-Cyano-5-{1-[3-({2-hydroxyethyl}amino)-propyl]-3-indolyl}-1-(1-methyl-3-indolyl)-2,3-dihydroimidazol-2-one
5-{1-[3-[({Benzo[1,3]dioxol-5-yl}methyl)-amino]propyl]-3-indolyl}-4-cyano-1-(1-methyl-3-indolyl)-2,3-dihydroimidazol-2-one
4-Cyano-1-(1-methyl-3-indolyl)-5-[1-[3-({3-propargyl}amino]-propyl)-3-indolyl]-2,3-dihydroimidazol-2-one 4-Cyano-1-(1-methyl-3-indolyl)-5-[1-[3-({3-pyridyl}methylamino]propyl)-3-indolyl]-2,3-dihydroimidazol-2-one 4-Cyano-5-[1-{3-([2-hydroxyethoxy]ethylamino)propyl}-3-indolyl]1-(1-methyl-3-indolyl)-3-indolyl]-2,3-dihydroimidazol-2-one 4-Cyano-1-(1-methyl-3-indolyl)-5-[1-(3-(2,2,2-trifluoroethylamino)propyl)-3-indolyl]-2,3-dihydroimidazol-2-one 4-Cyano-5-[1-(3-cyanopropyl)-3-indolyl]-1-(1-methyl-3-indolyl)-2,3-dihydroimidazol-2-one cis-5-[1-(4-Aminocyclohexyl)-3-indolyl]-4-cyano-1-(1-methyl-3-indolyl)-2,3-dihydroimidazol-2-one 5-[1-(4-Aminobutyl)-3-indolyl]-4-cyano-3-methyl-1-(1-propyl-3-indolyl)-2,3-dihydroimidazol-2-one 4-cyano-5-{1-[3-(guanidinomethyl)benzyl]-3-indolyl}-1-(1-methyl-3-indolyl)-2,3-dihydroimidazol-2-one 4-Cyano-1-(1-methyl-3-indolyl)-5-[1-((2S)-2-pyrrolidine-carbonyl)-3-indolyl]-2,3-dihydroimidazol-2-one 4-Cyano-1-(1-methyl-3-indolyl)-5-[1-((2R)-2-pyrrolidine-carbonyl)-3-indolyl]-2,3-dihydroimidazol-2-one 4-Cyano-1-(1-methyl-3-indolyl)-5-[(1S,3R)-1-(3-toluene-4-sulfonylamino)-cyclopentyl-methyl]-3-indolyl}-2,3-dihydroimidazol-2-one 5-{1-[1S,3R)-1-(3-Amino)cyclopentylmethyl]-3-indolyl}-4-cyano-1-(1-methyl-3-indolyl)-2,3-dihydroimidazol-2-one 4-Cyano-1-(1-methyl-3-indolyl)-5-[1-((2R)-2-pyrrolidinylmethyl)-3-indolyl]-2,3-dihydroimidazol-2-one 4-Cyano-5-[(1S,3S)-1-(3-N,N-dimethylaminocyclopentyl)-3-indolyl]-1-(1-methyl-3-indolyl)-2,3-dihydroimidazol-2-one, and 5-[1-(4-Aminobutyl)-3-indolyl]-4-cyano-1-(5,6-dichloro-1-methyl-3-indolyl)-2,3-dihydroimidazol-2-one
or a salt thereof.

10. A pharmaceutically acceptable salt of a compound as claimed in claim 1 or a pharmaceutically suitable salt thereof.

11. A pharmaceutical formulation comprising a compound as claimed in claim 1 or a pharmaceutically acceptable salt thereof, and a pharmaceutically acceptable adjuvant, diluent or carrier.

12. A process for the synthesis of a salt of a compound of formula (I) as defined in claim 1, comprising reacting a compound of formula (I) with an acid.

13. A process for the synthesis of a compound of formula (I) as defined in claim 1, comprising reacting a compound of formula (IV)

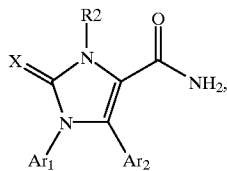

(IV)

wherein X, Ar$_1$, Ar$_2$ and R2 are as defined in claim 1, with a dehydrating agent.

14. A process for the synthesis of a compound of formula (II) or (III) as defined in claim 2, comprising reacting a compound of formula (V)

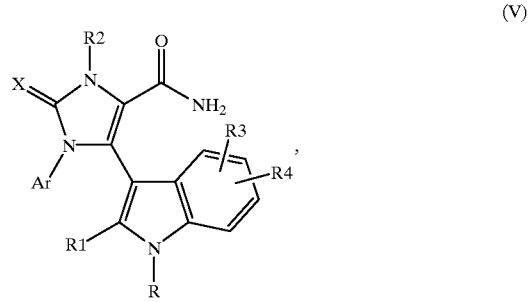

(V)

in which X, Ar, R and R1–R4 are as defined in claim 2, with a dehydrating agent.

15. A process for the synthesis of a compound of formula (V) as defined in claim 14, comprising reacting a compound of formula (VII)

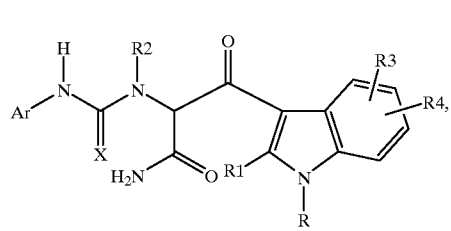

(VII)

in which X, Ar, R and R1–R4 are as defined in claim 2, with an acid at an elevated temperature.

16. A process according to claim 15, wherein the acid is acetic acid or scandium(III) trifluoromethane sulfonate and the elevated temperature range is from 105° C.–110° C.

17. A compound of formula (IX)

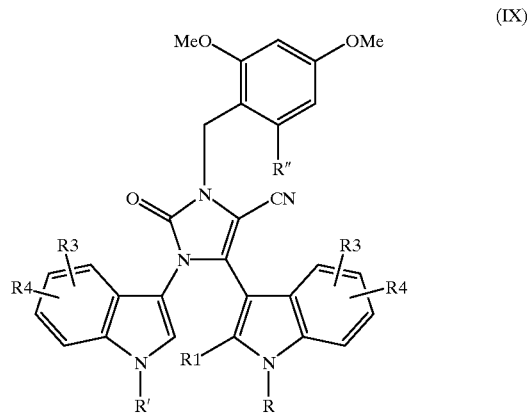

(IX)

in which R' is an alkyl group, R" is H or OMe, R is alkyl containing a protected amino or hydroxy group, R1 is H or C$_{1-3}$alkyl, R3 and R4 are each independently H, hydroxy, C$_{1-6}$alkyl, hydroxyC$_{1-6}$alkyl, haloC$_{1-6}$alkyl, C$_{1-3}$alkoxy, carboC$_{1-6}$alkoxy, halogen, nitrile, nitro or amino, or a salt or a solvate thereof, or a solvate of said salt.

18. A compound of formula (X)

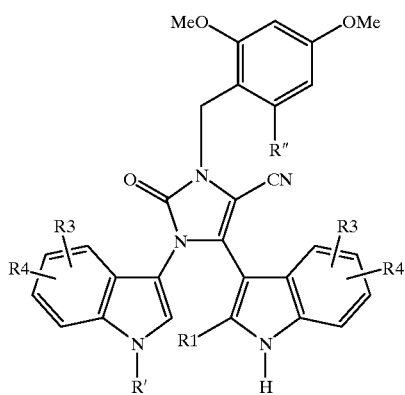

(X)

in which R' is an alkyl group, R" is H or OMe, R1 is H or $C_{1-3}$alkyl, R3 and R4 are each independently H, hydroxy, $C_{1-6}$alkyl, hydroxy$C_{1-6}$alkyl, halo$C_{1-6}$alkyl, $C_{1-3}$alkoxy, carbo$C_{1-6}$alkoxy, halogen, nitrile, nitro or amino,
or a salt or a solvate thereof, or a solvate of said salt.

19. A compound of formula (XI)

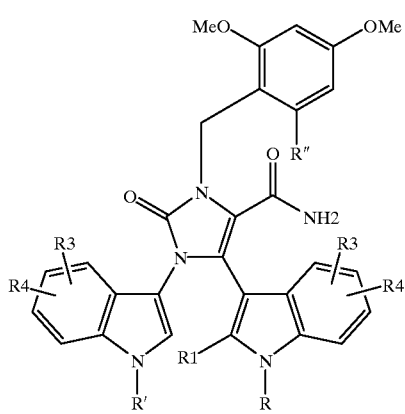

(XI)

in which R' is an alkyl group, R" is H or OMe, R1 is H or $C_{1-3}$alkyl, R3 and R4 are each independently H, hydroxy, $C_{1-6}$alkyl, hydroxy$C_{1-6}$alkyl, halo$C_{1-6}$alkyl, $C_{1-3}$alkoxy, carbo$C_{1-6}$alkoxy, halogen, nitrile, nitro or amino,
or a salt or a solvate thereof, or a solvate of said salt.

20. A compound of formula (XIII)

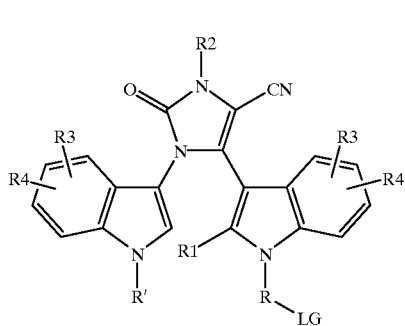

(XIII)

in which each of R' and R is an alkyl group, LG is a leaving group, R1 is H or $C_{1-3}$alkyl; R2 is H, $C_{1-3}$alkyl, hydroxy, amino, hydroxy$C_{1-3}$alkyl or amino$C_{1-3}$alkyl; and R3 and R4 are each independently H, hydroxy, $C_{1-6}$alkyl, hydroxy$C_{1-6}$alkyl, halo$C_{1-6}$alkyl, $C_{1-3}$alkoxy, carbo$C_{1-6}$alkoxy, halogen, nitrile, nitro or amino;
or a salt or a solvate thereof, or a solvate of said salt.

21. A compound of formula (XIV)

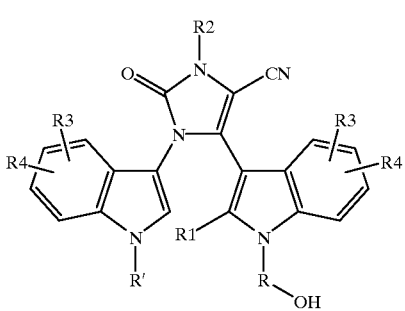

(XIV)

in which each of R' and R is an alkyl group, R1 is H or $C_{1-3}$alkyl; R2 is H, $C_{1-3}$alkyl, hydroxy, amino, hydroxy$C_{1-3}$alkyl or amino$C_{1-3}$alkyl; and R3 and R4 are each independently H, hydroxy, $C_{1-6}$alkyl, hydroxy$C_{1-6}$alkyl, halo$C_{1-6}$alkyl, $C_{1-3}$alkoxy, carbo$C_{1-6}$alkoxy, halogen, nitrile, nitro or amino;
or a salt or a solvate thereof, or a solvate of said salt.

22. A compound of formula (XV)

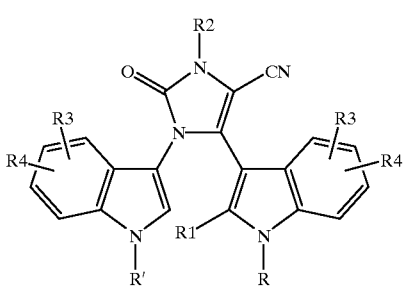

(XV)

in which R' is H or ethoxy carbonyl, R is an alkyl group containing a nitrile or primary amine, R1 is H or $C_{1-3}$alkyl; R2 is H, $C_{1-3}$alkyl, hydroxy, amino, hydroxy$C_{1-3}$alkyl or amino$C_{1-3}$alkyl; and R3 and R4 are each independently H, hydroxy, $C_{1-6}$alkyl, hydroxy$C_{1-6}$alkyl, halo$C_{1-6}$alkyl, $C_{1-3}$alkoxy, carbo$C_{1-6}$alkoxy, halogen, nitrile, nitro or amino;
or a salt or a solvate thereof, or a solvate of said salt.

23. A compound of formula (XVI)

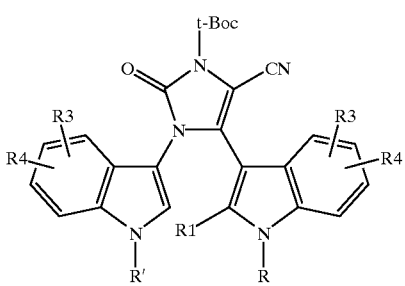

(XVI)

in which R' is an alkyl containing a protected amino group, R is an alkyl group, t-Boc is a t-butoxycarbonyl group, R1 is H or $C_{1-3}$alkyl; and R3 and R4 are each independently H, hydroxy, $C_{1-6}$alkyl, hydroxy$C_{1-6}$alkyl, halo$C_{1-6}$alkyl, $C_{1-3}$alkoxy, carbo$C_{1-6}$alkoxy, halogen, nitrile, nitro or amino;

or a salt or a solvate thereof, or a solvate of said salt.

24. A compound of formula (XVII)

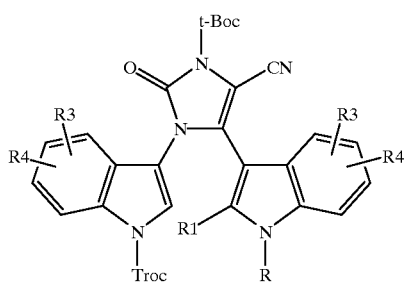

(XVII)

in which R is alkyl, Troc is a 2,2,2-trichloroethoxy carbonyl group, R1 is H or $C_{1-3}$alkyl; and R3 and R4 are each independently H, hydroxy, $C_{1-6}$alkyl, hydroxy$C_{1-6}$alkyl, halo$C_{1-6}$alkyl, $C_{1-3}$alkoxy, carbo$C_{1-6}$alkoxy, halogen, nitrile, nitro or amino;

or a salt or a solvate thereof, or a salt.

25. A method of treating inflammatory, immunological, bronchopulmonary, cardiovascular, oncological, or CNS-degenerative disorders, comprising administering to an individual in need thereof a therapeutically effective amount of a compound as claimed in claim 1 or a pharmaceutically acceptable salt thereof.

26. A compound according to claim 1, wherein one of $Ar_1$ or $Ar_2$ is an unsubstituted or substituted bicyclic heteroaromatic group.

27. A compound according to claim 1, wherein one of $Ar_1$ or $Ar_2$ is an unsubstituted or substituted indole.

28. A compound according to claim 2, in which R is aminoethyl, aminopropyl, aminobutyl, aminocyclopentyl, guanidinopropyl, amidinobutyl ,or amidinothiopropyl.

29. A process for the synthesis of a compound of formula (II) or (III) as defined in claim 2, comprising reacting a compound of formula (V)

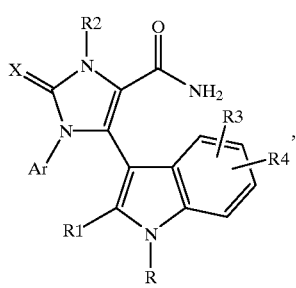

(V)

in which X, Ar, R and R1–R4 have been defined in claim 2 and at least one of Ar, R and R1–R4 contains a protecting group, with a dehydrating agent to form a protected compound of formula (V), and deprotecting the protected compound of formula (V).

30. A process for the synthesis of a compound of formula (II) or (III) as defined in claim 2, comprising reacting a compound of formula (V)

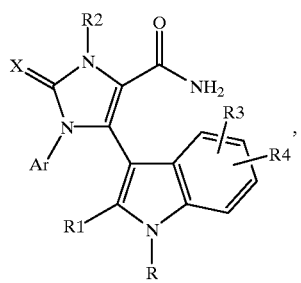

(V)

in which X, Ar, R and R1–R4 have been defined in claim 2 and at least one of R, R2 or Ar contains a protected amino group or a protected hydroxy group, with a dehydrating agent to form a protected compound of formula (V), and deprotecting the protected compound of formula (V).

31. A process for the synthesis of a compound of formula (II) or (III)

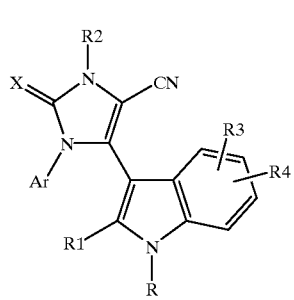

(II)

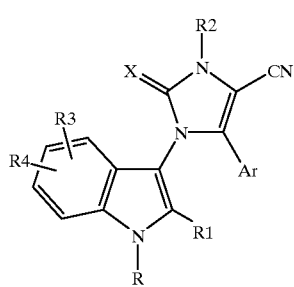

(III)

wherein:

Ar is an indolyl substituted at the indolyl nitrogen atom with an alkyl group;

X is O;

R is an alkyl containing an amino or hydroxy group;

R1 is H or $C_{1-3}$alkyl;

R2 is H; and

R3 and R4 are each independently H, hydroxy, C$_{1-6}$alkyl, hydroxyC$_{1-6}$alkyl, haloC$_{1-6}$alkyl, C$_{1-3}$alkoxy, carboC$_{1-6}$alkoxy, halogen, nitrile, nitro or amino, comprising reacting a compound of formula (IX)

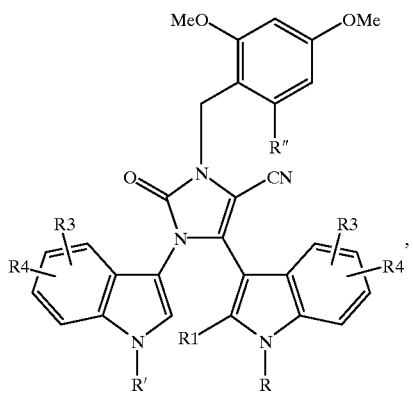
(IX)

in which R' is an alkyl group, R" is H or OMe, R is alkyl containing a protected amino or hydroxy group, and R1, R3 and R4 are as defined in claim 2, with a deprotecting agent.

32. A process for the synthesis of a compound of formula (IX) as defined in claim 31, comprising reacting a compound of formula (X)

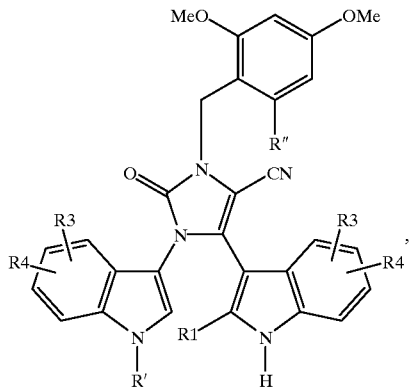
(X)

in which R' is an alkyl group, R" is H or OMe, and R1, R3 and R4 are as defined in claim 2, with an alkylating agent in the presence of a base.

33. The process of claim 32, wherein the alkylating agent is an alkyl halide containing a protected amino or hydroxy group.

34. A process for the synthesis of a compound of formula (X) as defined in claim 32, comprising reacting a compound of formula (XI)

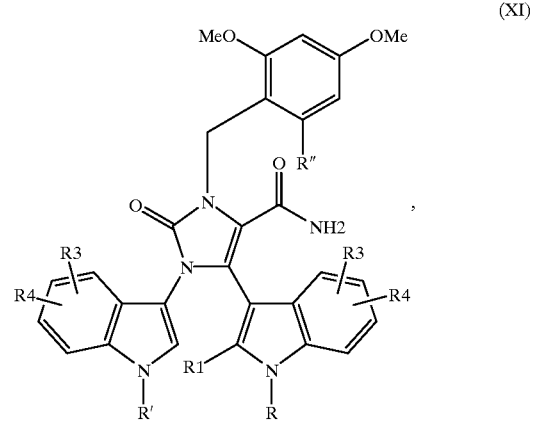
(XI)

in which R' is an alkyl group, R" is H or OMe, and R1, R3 and R4 are as defined in claim 2, with a dehydrating agent.

35. A process for the synthesis of a compound of formula (XI) as defined in claim 34, comprising reacting a compound of formula (XII)

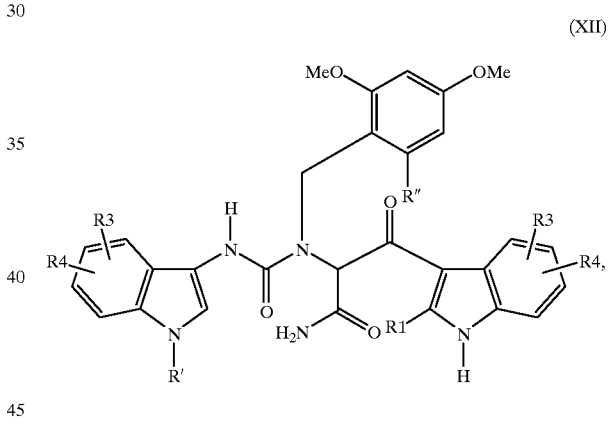
(XII)

in which R' is an alkyl group, R" is H or OMe, and R1, R3 and R4 are as defined in claim 2, with an acid.

36. A process for the synthesis of a compound of formula (II) or (III)

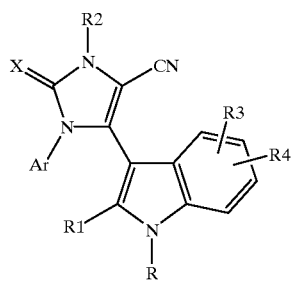
(II)

-continued

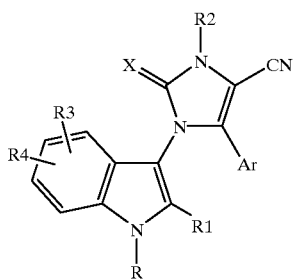
(III)

wherein:
Ar is an indolyl substituted at the indole nitrogen atom with an alkyl group;
X is O;
R is is an alkyl containing a thioamidino, monoalkyl amino or dialkyl amino;
R1 is H or $C_{1-3}$alkyl;
R2 is H, $C_{1-3}$alkyl, hydroxy, amino, hydroxy$C_{1-3}$alkyl or amino$C_{1-3}$alkyl; and
R3 and R4 are each independently H, hydroxy, $C_{1-6}$alkyl, hydroxy$C_{1-6}$alkyl, halo$C_{1-6}$alkyl, $C_{1-3}$alkoxy, carbo$C_{1-6}$alkoxy, halogen, nitrile, nitro or amino, comprising reacting a compound of formula (XIII)

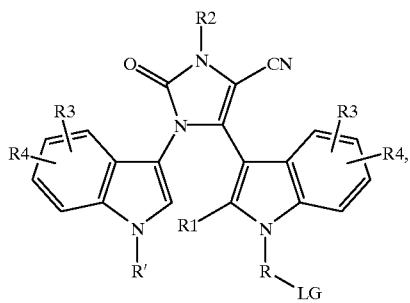
(XIII)

in which each of R' and R is an alkyl group, LG is a leaving group, and R1–R4 are as defined in claim 2, with thiourea, or a monoalkyl or dialkyl amine.

37. The process of claim 36, wherein the leaving group is a sulfonic ester.

38. The process of claim 37, wherein the leaving group is mesylate.

39. A process for the synthesis of a compound of formula (XIII) as defined in claim 36, comprising reacting a compound of formula (XIV)

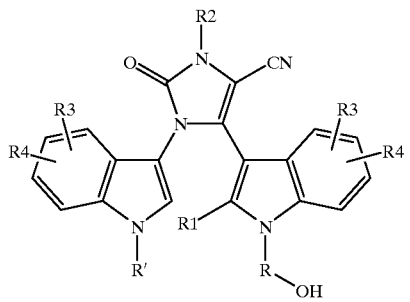
(XIV)

in which each of R' and R is an alkyl group and R1–R4 are as defined in claim 2, with a sulfonic acid halide.

40. The process of claim 39, wherein the sulfonic acid halide is mesyl chloride.

41. A process for the synthesis of a compound of formula (II) or (III)

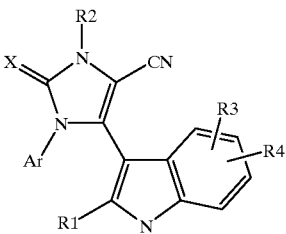
(II)

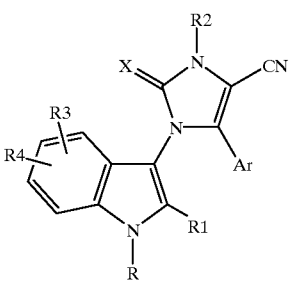
(III)

wherein:

Ar is indolyl;

X is O or S;

R is alkyl containing an amidino or a guanidino group;

R1 is H or $C_{1-3}$alkyl;

R2 is H, $C_{1-3}$alkyl, hydroxy, amino, hydroxy$C_{1-3}$alkyl or amino$C_{1-3}$alkyl; and R3 and R4 are each independently H, hydroxy, $C_{1-6}$alkyl, hydroxy$C_{1-6}$alkyl, halo$C_{1-6}$alkyl, $C_{1-3}$alkoxy, carbo$C_{1-6}$alkoxy, halogen, nitrile, nitro or amino, comprising reacting a compound of formula (II), in which Ar is indolyl with the indole nitrogen atom being protected and R is an alkyl group containing a nitrile, with hydrogen chloride in ethanol, followed by reacting with ammonia in methanol to form the compound of formula (II) or (III) wherein R is alkyl containing an amidino group; or reacting a compound of formula (II), in which Ar is indolyl with the indole nitrogen atom being protected and R is an alkyl group containing a primary amine, with 3,5-dimethylpyrazole-1-carboxamidinium nitrate in refluxing ethanol in the presence of a base to form the compound of formula (II) or (III) wherein R is alkyl containing an guanidino group.

42. A process for the synthesis of a compound of formula (II) or (III)

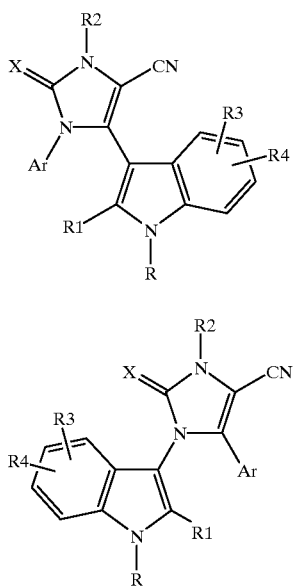

(II)

(III)

wherein:
Ar is indolyl substituted at the indole nitrogen atom with an aminoalkyl group;
X is O;
R is alkyl;
R1 is H or $C_{1-3}$alkyl;
R2 is H; and
R3 and R4 are each independently H, hydroxy, $C_{1-6}$alkyl, hydroxy$C_{1-6}$alkyl, halo$C_{1-6}$alkyl, $C_{1-3}$alkoxy, carbo$C_{1-6}$alkoxy, halogen, nitrile, nitro or amino, comprising reacting a compound of formula (XVI)

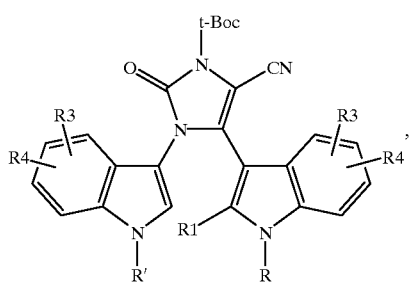

(XVI)

in which R' is a protected aminoalkyl group, R is an alkyl group, t-Boc is a t-butoxycarbonyl group, and R1, R3 and R4 are as defined in claim 2, with an acid to form the compound of formula (II) or (III).

43. A process for the synthesis of a compound of formula (XVI) as defined in claim 42, comprising reacting a compound of formula (XVII)

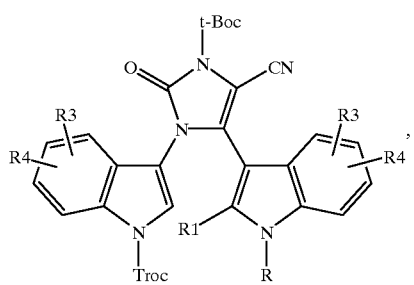

(XVII)

in which R is alkyl, Troc is a 2,2,2-trichloroethoxy carbonyl group, and R1, R3 and R4 are as defined in claim 2, with cadmium in an acid and an organic solvent to form an intermediate of the following formula

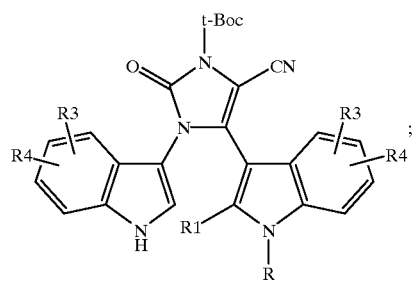

and reacting the intermediate with an alkylating agent containing a protected aminoalkyl group.

44. A composition comprising a compound of claim 1 or a salt thereof and a pharmaceutically acceptable adjuvant or a carrier.

45. A method of inhibiting protein kinase C in an individual comprising administering to the individual a therapeutically effective amount of a compound as claimed in claim 1 or a pharmaceutically acceptable salt thereof.

* * * * *